US012780809B2

(12) United States Patent
Li et al.

(10) Patent No.: US 12,780,809 B2
(45) Date of Patent: Nov. 3, 2026

(54) 8-(PICOLINAMIDE) SUBSTITUTED COUMARIN COMPOUND, AND PREPARATION METHOD THEREFOR AND USE THEREOF

(71) Applicant: LONGIVITRON (SUZHOU) BIOTECHNOLOGY CO., LTD, Jiangsu (CN)

(72) Inventors: Yan Li, Jiangsu (CN); Xiaoguang Chen, Jiangsu (CN); Xiaoxi Zhang, Jiangsu (CN)

(73) Assignee: Longivitron (Suzhou) Biotechnology Co., Ltd., Jiangsu (CN)

( * ) Notice: Subject to any disclaimer, the term of this patent is extended or adjusted under 35 U.S.C. 154(b) by 492 days.

(21) Appl. No.: 18/548,988

(22) PCT Filed: Feb. 24, 2022

(86) PCT No.: PCT/CN2022/077640
§ 371 (c)(1),
(2) Date: Sep. 5, 2023

(87) PCT Pub. No.: WO2022/183963
PCT Pub. Date: Sep. 9, 2022

(65) Prior Publication Data
US 2024/0174650 A1 May 30, 2024

(30) Foreign Application Priority Data
Mar. 5, 2021 (CN) ........................ 202110246184.X

(51) Int. Cl.
*C07D 405/12* (2006.01)
*A61P 25/16* (2006.01)
*C07D 405/14* (2006.01)

(52) U.S. Cl.
CPC ............ *C07D 405/12* (2013.01); *A61P 25/16* (2018.01); *C07D 405/14* (2013.01)

(58) Field of Classification Search
None
See application file for complete search history.

(56) References Cited

U.S. PATENT DOCUMENTS

2012/0165330 A1 6/2012 Vu

FOREIGN PATENT DOCUMENTS

| | | | |
|---|---|---|---|
| CN | 106496132 | A | 3/2017 |
| CN | 108309982 | A | 7/2018 |
| CN | 109293606 | A | 2/2019 |
| CN | 110551048 | A | 12/2019 |
| CN | 112939955 | A | 6/2021 |
| JP | 2011519863 | A | 7/2011 |
| JP | 2012504149 | A | 2/2012 |
| WO | 2014100833 | A1 | 6/2014 |
| WO | 2016067012 | A1 | 5/2016 |
| WO | 2017156181 | A1 | 9/2017 |
| WO | 2018068357 | A1 | 4/2018 |
| WO | 2018085348 | A1 | 5/2018 |

OTHER PUBLICATIONS

Machine-generated English translation of Chinese Patent No. CN112939955, published on Jun. 11, 2021.*
Cui et al., "Discovery of Potent and Selective Sirtuin 2 (SIRT2) Inhibitors Using a Fragment-Based Approach", Journal of Medicinal Chemistry, 2014, 57, 8340-8357.*
Xue et al., "Structure, functions, and recent advances in the development of SIRT2 inhibitors", Pharmaceutical Science Advances, 2023, 1, p. 1-12.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Office Action of Prior Chinese Application No. 202110246184.X dated May 13, 2022, 8 pages.
Schiedel, et al., "Fluorescence-Based Screening Assays for the NAD+-Dependent Histone Deacetylase smSirt2 from Schistosoma mansoni", Journal of Biomolecular Screening, vol. 20, No. 1, 2015, pp. 112-121.

(Continued)

*Primary Examiner* — Po-Chih Chen
(74) *Attorney, Agent, or Firm* — DINSMORE & SHOHL LLP

(57) ABSTRACT

Disclosed are an 8-(picolinamide) substituted coumarin compound, and a preparation method therefor and the use thereof, wherein the structure of the 8-(picolinamide) substituted coumarin compound is represented by formula (I), and a ring A is independently selected from a group composed of phenyl, naphthyl and a 5-14 membered aromatic heterocyclyl. The 8-(picolinamide) substituted coumarin compound disclosed in the present invention is of a brand-new compound structure and has a strong SIRT2 inhibitory activity, wherein the in-vitro SIRT2 inhibitory activity IC50 of 18 compounds reaches a micromolar level, and the 8-(picolinamide) substituted coumarin compound has a significant protective effect on neuroma cells. Therefore, the compound can be widely used for preparing drugs for treating and/or preventing diseases or conditions related to excessive SIRT2 activity or overexpression of SIRT2, or preparing drugs for treating and/or preventing Parkinson's disease, metabolic diseases and tumors.

11 Claims, 1 Drawing Sheet

Specification includes a Sequence Listing.

(56) References Cited

OTHER PUBLICATIONS

Rotili, et al., "Simplification of the tetracyclic SIRT1-selective inhibitor MC2141: Coumarin- and pyrimidine-based SIRT1/2 inhibitors with different selectivity profile", Bioorganic & Medicinal Chemistry, 2011, pp. 3659-3668.
International Search Report of Corresponding International Application No. PCT/CN2022/077640 mailed May 26, 2022, 8 pages.

* cited by examiner

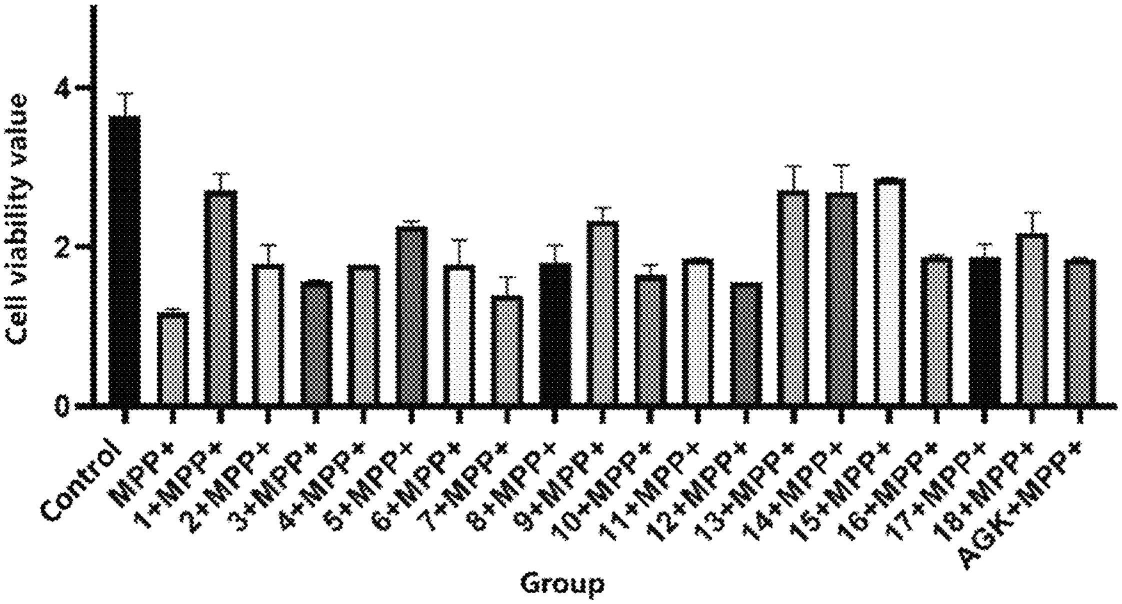
Cell viability value
4
2
0
Control
MPP+
1+MPP+
2+MPP+
3+MPP+
4+MPP+
5+MPP+
6+MPP+
7+MPP+
8+MPP+
9+MPP+
10+MPP+
11+MPP+
12+MPP+
13+MPP+
14+MPP+
15+MPP+
16+MPP+
17+MPP+
18+MPP+
AGK+MPP+
Group

8-(PICOLINAMIDE) SUBSTITUTED COUMARIN COMPOUND, AND PREPARATION METHOD THEREFOR AND USE THEREOF

This application is a U.S. National Phase Entry of International Application No. PCT/CN2022/077640, entitled S"8-(PICOLINAMIDE) SUBSTITUTED COUMARIN COMPOUND, AND PREPARATION METHOD THEREFOR AND USE THEREOF" and filed Feb. 24, 2022, which claims priority to Chinese Patent Application No. 202110246184.X filed Mar. 5, 2021.

TECHNICAL FIELD

The present application belongs to the technical field of pharmaceuticals, and specifically relates to an 8-(picolinamide)-substituted coumarin compound and a preparation method therefor and use thereof, and in particular to an 8-(picolinamide)-substituted coumarin compound capable of inhibiting the activity or expression of Sirtuin 2 (also called as SIRT2), a preparation method therefor and use thereof.

BACKGROUND

Parkinson□s disease is a common neurodegenerative disease, the cardinal clinical manifestation of which includes bradykinesia, rigidity and resting tremor. The pathologic change of Parkinson□s disease is mainly characterized by the degeneration of dopaminergic neurons in the substantia nigra of the midbrain and the marked reduction of dopamine level accordingly in striatum. Patients with Parkinson||s disease bear a heavy physical and psychological burden. However, there are no drugs that can protect the neurons in Parkinson□s disease from the degenerative lesions. The therapeutic drugs commercially available for Parkinson□s disease (for example, levodopa) are mainly aimed at relieving the symptoms, and long-term use of such drugs will bring serious side effects to patients. Therefore, it is of great importance to explore new treatments and develop new therapeutic drugs for Parkinson□s disease.

Sirtuin is a type of histone acetyltransferases, whose enzymatic activity is mainly characterized by the removal of acetyl groups from lysine residues in histones or other proteins. In this process, Sirtuin depends on nicotinamide adenine dinucleotide ($NAD^+$) as one of the substrates. The gene sequences of the Sirtuin family are relatively conserved across species. Crystallographic structure studies have shown that Sirtuin consists of two domains, a larger one and a smaller one. The larger domain has relatively conserved sequence and has the characteristics of NAD and NADP binding enzymes. In contrast, the sequence of the smaller domain is more variable. The active center of Sirtuin is located in the cleft between the larger and smaller domains. The human Sirtuin family consists of seven members: SIRT1-7, which have different subcellular localizations and target different substrates, including p53, α-tubulin, FOXO, etc., to achieve different biological modulation functions. The biological functions of Sirtuin are the hotspot of the current research in life medicine, which are mainly reflected in the metabolism, aging, longevity, stress response, genome stability and the like.

As an important member of the Sirtuin family, SIRT2 is predominantly found in the cytoplasm, and its target protein substrates include α-tubulin, histone H4, p53, FOXO, and 14-3-3 protein. Functional studies of SIRT2 have shown that SIRT2 regulates the cellular mitosis progression through the deacetylation of H4-K16; SIRT2 maintains genome stability through activating the anaphase promoting complex/cyclosome (APC/C) system; SIRT2 regulates cell necrosis through mediating the interactions of Receptor-interacting proteins 1 and 3 (RIP1 and RIP3). Recent studies have shown that inhibition of SIRT2 activity has potential value in the treatment of Parkinson□s disease, specifically: (1) SIRT2 is expressed in high abundance in the central nervous system of the adult brain and regulates the related physiological metabolism; (2) siRNA and the small molecule inhibitor AGK2 of SIRT2 are able to decreased the neuronal cytotoxicity caused by α-synulein, and AGK2 is also able to dose-dependently protect the transgenic Parkinson□s drosophila model from neuronal apoptosis in vivo; (3) SIRT2 deacetylates FOXO3a to increase the expression of Bim at RNA and protein levels, which contributes to the apoptosis activated by N-methyl-4-phenyl-1,2,3,6-tetrahydropyridine (MPTP) in the Parkinson□s disease cell model and in the mouse model brain. However, the brains of mice knocked SIRT2 gene out show obvious nigrostriatal damage reduction; (4) in addition, AK-7, a small molecule inhibitor of SIRT2, is able to significantly reduce the aggregation of mutant huntingtin in the brains of transgenic mice with Huntington||s disease, another neurodegenerative disease, and also significantly improves the behavioral performance of Huntington| s transgenic mice and prolongs their survival time. Representative small molecule inhibitors of SIRT2 in the prior art include the following:

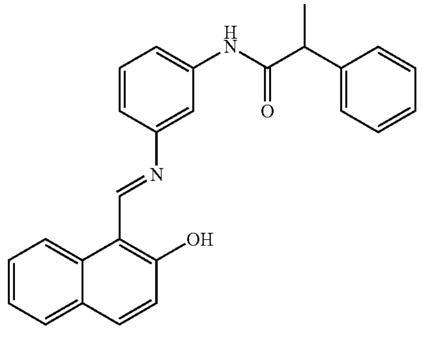

Sirtinol
SIRT1 $IC_{50}$=131 μM
SIRT2 $IC_{50}$=58 μM

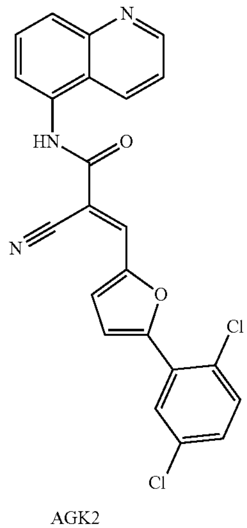

AGK2
SIRT2 $IC_{50}$=3.5 μM

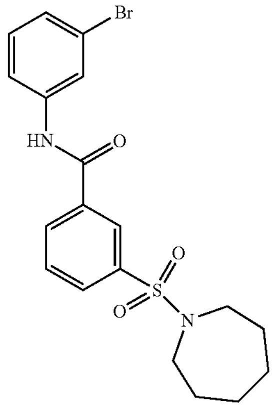

AK-7
SIRT2 $IC_{50}$=15.5 μM

-continued

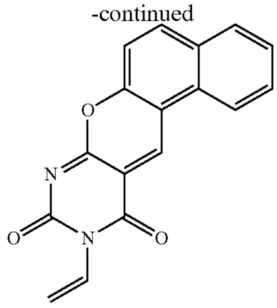

Benzodeazaoxaflavin
SIRT1 $IC_{50}$=6.6 μM
SIRT2 $IC_{50}$=10.8 μM

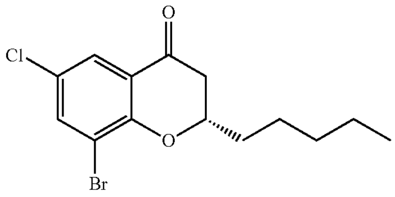

Chroman-4-one derivative
SIRT2 $IC_{50}$=1.5 μM

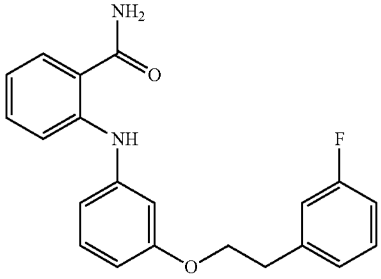

2-Anilinobenzamide derivatives
SIRT1 $IC_{50}$>300 μM
SIRT2 $IC_{50}$=0.57 μM
SIRT3 $IC_{50}$>300 μM In view of the potential activity of SIRT2 small molecule inhibitors in the treatment of Parkinson's disease, the design and synthesis of new SIRT2 inhibitors has been one of the hotspots of current research.

SUMMARY

In view of the shortcomings of the prior art, the present application is to provide an 8-(picolinamide)-substituted coumarin compound and a preparation method therefor and use thereof, and especially, to provide an 8-(picolinamide)-substituted coumarin compound capable of inhibiting the activity or expression of SIRT2, and a preparation method therefor and use thereof. The present application develops a type of 8-(picolinamide)-substituted coumarin compound with novel structure, which have significant SIRT2 inhibitory activity and good selectivity for SIRT2, and which can be used in treating and/or preventing Parkinson's disease, metabolic disease, tumor and the like.

In order to achieve the object of the present application, the present application adopts the technical solutions below.

In a first aspect, the present application provides an 8-(picolinamide)-substituted coumarin compound, and the 8-(picolinamide)-substituted coumarin compound has a structure shown in Formula (I):

Formula (I)

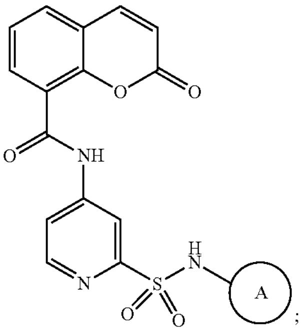

;

wherein ring A is independently selected from the group consisting of: phenyl, naphthyl and a 5-14-membered aromatic heterocyclic group (for example, a 5-membered aromatic heterocyclic group, a 6-membered aromatic heterocyclic group, a 7-membered aromatic heterocyclic group, a 8-membered aromatic heterocyclic group, a 9-membered aromatic heterocyclic group, a 10-membered aromatic heterocyclic group, a 11-membered aromatic heterocyclic group, a 12-membered aromatic heterocyclic group, a 13-membered aromatic heterocyclic group, and a 14-membered aromatic heterocyclic group);

the phenyl, naphthyl and 5-14-membered aromatic heterocyclic group are unsubstituted or substituted with one to five (for example, 1, 2, 3, 4, and 5) $R_a$; each $R_a$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-8}$ alkoxy, $C_{1-8}$ alkylcarbonyl, $C_{1-8}$ alkoxycarbonyl, $C_{1-8}$ alkyl, $C_{3-8}$ cycloalkyl and phenyl;

for the $R_a$, the $C_{1-8}$ alkyl, $C_{3-8}$ cycloalkyl and phenyl are unsubstituted or substituted by one to five (for example, 1, 2, 3, 4, and 5) $R_b$; each $R_b$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino and $C_{1-8}$ alkylcarbonyl.

The $C_{1-8}$ means that the number of carbon atoms of the substituent is 1, 2, 3, 4, 5, 6, 7, or 8; the $C_{3-8}$ means that the number of carbon atoms of the substituent is 3, 4, 5, 6, 7, or 8.

The 8-(picolinamide)-substituted coumarin compound involved in the present application is a new compound structure and has an in vitro SIRT2 inhibitory activity of 50% or more, wherein eighteen of the compounds have an in vitro SIRT2 inhibitory activity ($IC_{50}$) at micromolar level, and in particular eleven of the compounds have $IC_{50}$ values at $10^{-7}$ mol/L level, and four of the compounds have $IC_{50}$ values at $10^{-8}$ mol/L level, showing good SIRT2 inhibitory activity and significant protective effect on neuroblastoma cells. Hence, the 8-(picolinamide)-substituted coumarin compound can be widely used in the preparation of a drug for treating and/or preventing a disease or a disorder associated with excessive SIRT2 activity or SIRT2 overexpression or in the preparation of a drug for treating and/or preventing Parkinson's disease, metabolic disease, or tumor.

Preferably, in Formula (I), ring A is independently selected from the group consisting of: phenyl, naphthyl and a 5-14-membered aromatic heterocyclic group (for example, a 5-membered aromatic heterocyclic group, a 6-membered aromatic heterocyclic group, a 7-membered aromatic heterocyclic group, a 8-membered aromatic heterocyclic group, a 9-membered aromatic heterocyclic group, a 10-membered aromatic heterocyclic group, a 11-membered aromatic heterocyclic group, a 12-membered aromatic heterocyclic group, a 13-membered aromatic heterocyclic group, and a 14-membered aromatic heterocyclic group);

the phenyl, naphthyl and 5-14-membered aromatic heterocyclic group are unsubstituted or substituted with one to five (for example, 1, 2, 3, 4, or 5) $R_a$; each $R_a$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-6}$ alkoxy, $C_{1-6}$ alkylcarbonyl, $C_{1-6}$ alkoxycarbonyl, $C_{1-6}$ alkyl, $C_{3-6}$ cycloalkyl and phenyl;

for the $R_a$, the $C_{1-6}$ alkyl, $C_{3-6}$ cycloalkyl and phenyl are unsubstituted or substituted by one to five (for example, 1, 2, 3, 4, or 5) $R_b$; each $R_b$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino and $C_{1-6}$ alkylcarbonyl.

The $C_{1-6}$ means that the number of carbon atoms of the substituent is 1, 2, 3, 4, 5, or 6; the $C_{3-6}$ means that the number of carbon atoms of the substituent is 3, 4, 5, or 6.

Preferably, the 8-(picolinamide)-substituted coumarin compound has a structure shown in Formula (IA):

Formula (IA)

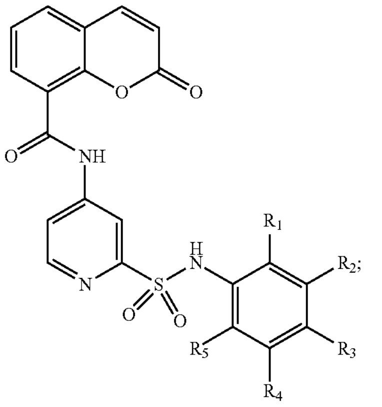

wherein $R_1$, $R_2$, $R_3$, $R_4$ and $R_5$ are each independently selected from the group consisting of: hydrogen, deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-4}$ alkoxy, $C_{1-4}$ alkylcarbonyl, $C_{1-4}$ alkoxycarbonyl, $C_{1-4}$ alkyl and phenyl.

The $C_{1-4}$ means that the number of carbon atoms of the substituent is 1, 2, 3, or 4.

Preferably, the 8-(picolinamide)-substituted coumarin compound has a structure shown in Formula (IB):

Formula (IB)

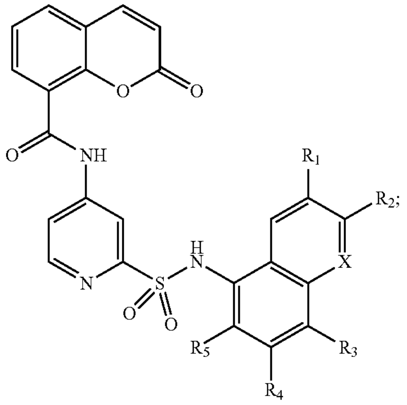

wherein $R_1$, $R_2$, $R_3$, $R_4$ and $R_5$ are each independently selected from the group consisting of: hydrogen, deuterium, halogen, hydroxyl, sulfhydryl, amino, cyano, nitro, methanesulfonyl, trifluoromethyl, trifluoromethoxy, formylamino, $C_{1-4}$ alkoxy, $C_{1-4}$ alkylcarbonyl and $C_{1-4}$ alkyl; X is independently selected from N or C.

The $C_{1-4}$ means that the number of carbon atoms of the substituent is 1, 2, 3, or 4.

Further preferably, the 8-(picolinamide)-substituted coumarin compound is selected from structures shown as follows (represented by structural formula and systematic name, respectively):

1

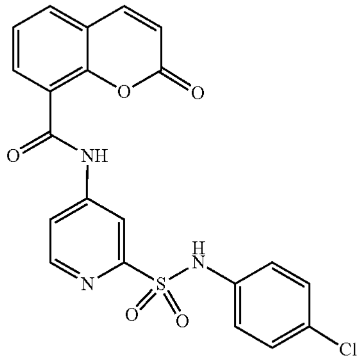 [SMILES: O=C(Nc1ccnc(S(=O)(=O)Nc2ccc(Cl)cc2)c1)c1cccc2ccc(=O)oc12]

N-(2-(N-(4-chlorophenyl)aminosulfonyl)-pyridin-4-yl)-2-oxo-2H-chromene-8-amide

-continued
2
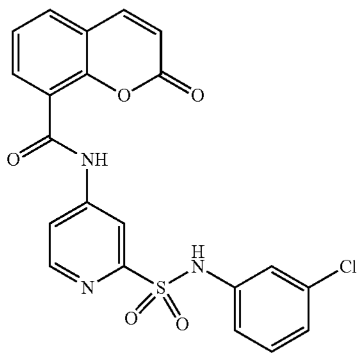 [SMILES: O=C(Nc1ccnc(S(=O)(=O)Nc2cccc(Cl)c2)c1)c1cccc2ccc(=O)oc12]
N-(2-(N-(3-chlorophenyl)amino-sulfonyl)-pyridin-4-yl)-2-oxo-2H-chromene-8-amide
3
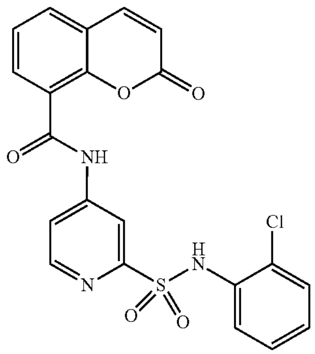 [SMILES: O=C(Nc1ccnc(S(=O)(=O)Nc2ccccc2Cl)c1)c1cccc2ccc(=O)oc12]
N-(2-(N-(2-chlorophenyl)amino-sulfonyl)-pyridin-4-yl)-2-oxo-2H-chromene-8-amide
4
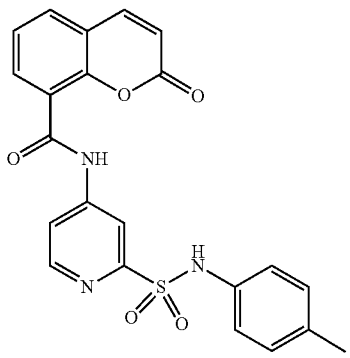 [SMILES: Cc1ccc(NS(=O)(=O)c2cc(NC(=O)c3cccc4ccc(=O)oc34)ccn2)cc1]
N-(2-(N-(4-methylphenyl)amino-sulfonyl)-pyridin-4-yl)-2-oxo-2H-chromene-8-amide
5
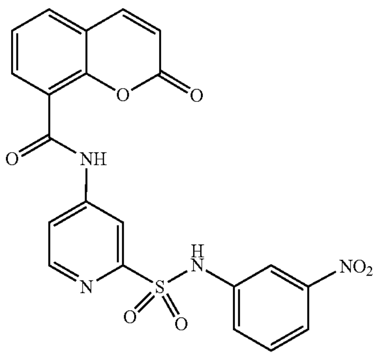 [SMILES: O=C(Nc1ccnc(S(=O)(=O)Nc2cccc([N+](=O)[O-])c2)c1)c1cccc2ccc(=O)oc12]
N-(2-(N-(3-nitrophenyl)aminosulfonyl)-pyridin-4-yl)-2-oxo-2H-chromene-8-amide -continued
| | | |
|---|---|---|
| 6 | 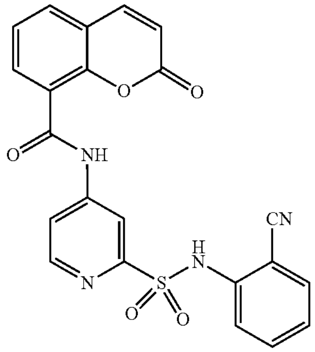 [SMILES: N#Cc1ccccc1NS(=O)(=O)c1cc(NC(=O)c2cccc3ccc(=O)oc23)ccn1] | N-(2-(N-(2-cyanophenyl)amino-sulfonyl)-pyridin-4-yl)-2-oxo-2H-chromene-8-amide |
| 7 | 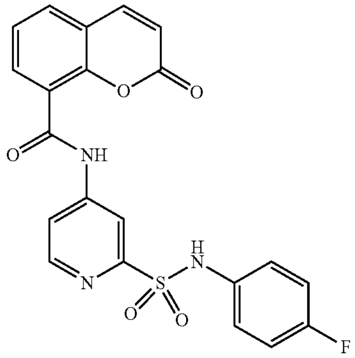 [SMILES: O=C(Nc1ccnc(S(=O)(=O)Nc2ccc(F)cc2)c1)c1cccc2ccc(=O)oc12] | N-(2-(N-(4-fluorophenyl)amino-sulfonyl)-pyridin-4-yl)-2-oxo-2H-chromene-8-amide |
| 8 | 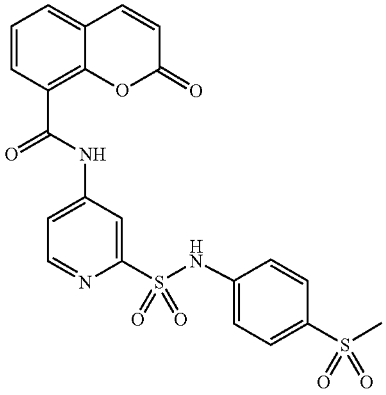 [SMILES: CS(=O)(=O)c1ccc(NS(=O)(=O)c2cc(NC(=O)c3cccc4ccc(=O)oc34)ccn2)cc1] | N-(2-(N-(4-methylsulfonylphenyl) aminosulfonyl)-pyridin-4-yl)-2-oxo-2H-chromene-8-amide |
| 9 | 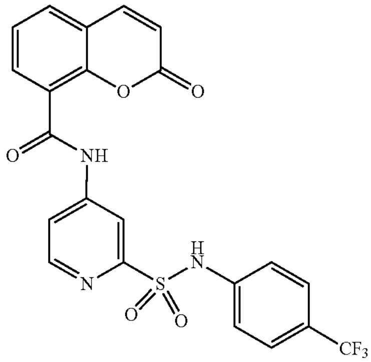 [SMILES: O=C(Nc1ccnc(S(=O)(=O)Nc2ccc(C(F)(F)F)cc2)c1)c1cccc2ccc(=O)oc12] | N-(2-(N-(4-trifluoromethylphenyl) aminosulfonyl)-pyridin-4-yl)-2-oxo-2H-chromene-8-amide |

-continued
10 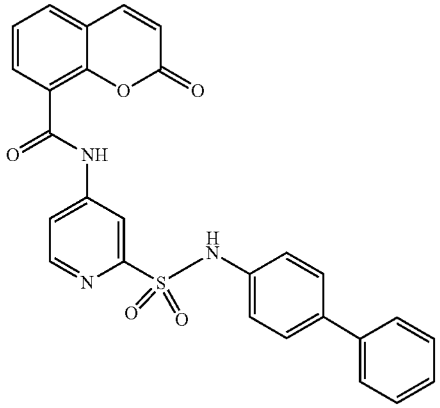 [SMILES: O=C(Nc1ccnc(S(=O)(=O)Nc2ccc(-c3ccccc3)cc2)c1)c1cccc2ccc(=O)oc12]
N-(2-(N-(4-phenylphenyl)amino-sulfonyl)-pyridin-4-yl)-2-oxo-2H-chromene-8-amide
11 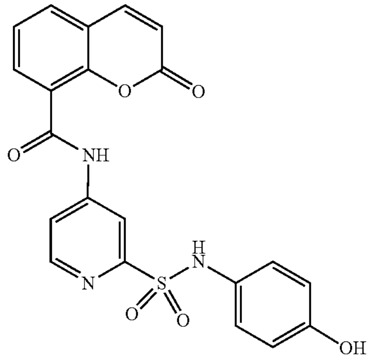 [SMILES: O=C(Nc1ccnc(S(=O)(=O)Nc2ccc(O)cc2)c1)c1cccc2ccc(=O)oc12]
N-(2-(N-(4-hydroxyphenyl)amino-sulfonyl)-pyridin-4-yl)-2-oxo-2H-chromene-8-amide
12 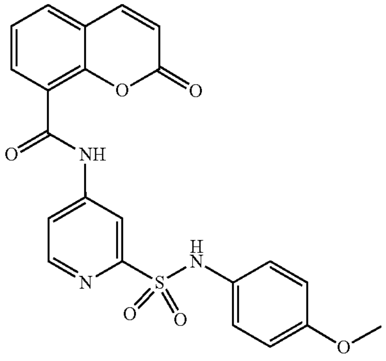 [SMILES: COc1ccc(NS(=O)(=O)c2cc(NC(=O)c3cccc4ccc(=O)oc34)ccn2)cc1]
N-(2-(N-(4-methoxylphenyl)amino-sulfonyl)-pyridin-4-yl)-2-oxo-2H-chromene-8-amide
13 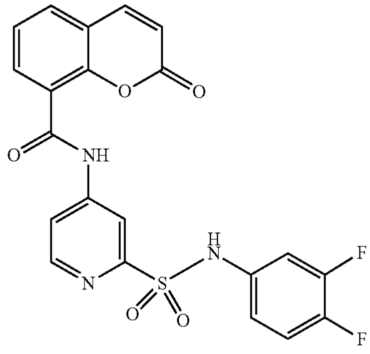 [SMILES: O=C(Nc1ccnc(S(=O)(=O)Nc2ccc(F)c(F)c2)c1)c1cccc2ccc(=O)oc12]
N-(2-(N-(3,4-difluorophenyl)amino-sulfonyl)-pyridin-4-yl)-2-oxo-2H-chromene-8-amide -continued
14 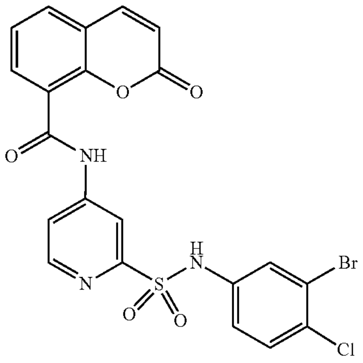 [SMILES: O=C(Nc1ccnc(S(=O)(=O)Nc2ccc(Cl)c(Br)c2)c1)c1cccc2ccc(=O)oc12]
N-(2-(N-(3-bromo-4-chlorophenyl) aminosulfonyl)-pyridin-4-yl)-2-oxo-2H-chromene-8-amide
15 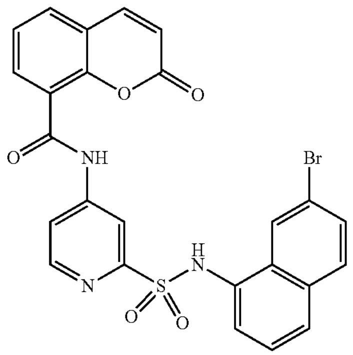 [SMILES: O=C(Nc1ccnc(S(=O)(=O)Nc2cccc3ccc(Br)cc23)c1)c1cccc2ccc(=O)oc12]
N-(2-(N-(7-bromonaphth-1-yl)amino-sulfonyl)-pyridin-4-yl)-2-oxo-2H-chromene-8-amide
16 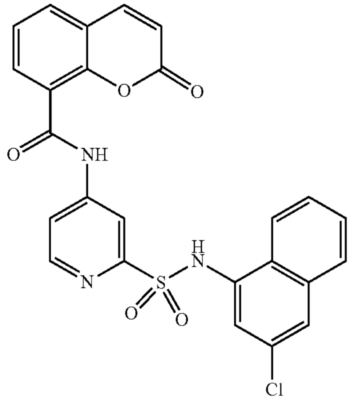 [SMILES: O=C(Nc1ccnc(S(=O)(=O)Nc2cc(Cl)cc3ccccc23)c1)c1cccc2ccc(=O)oc12]
N-(2-(N-(3-chloronaphth-1-yl)amino-sulfonyl)-pyridin-4-yl)-2-oxo-2H-chromene-8-amide
17 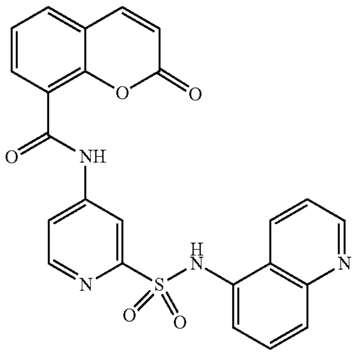 [SMILES: O=C(Nc1ccnc(S(=O)(=O)Nc2cccc3ncccc23)c1)c1cccc2ccc(=O)oc12]
N-(2-(N-(quinoline-5-yl)aminosulfonyl)-pyridin-4-yl)-2-oxo-2H-chromene-8-amide -continued 18 N-(2-(N-(7-bromo-quinoline-5-yl) aminosulfonyl)-pyridin-4-yl)-2-oxo-2H-chromene-8-amide

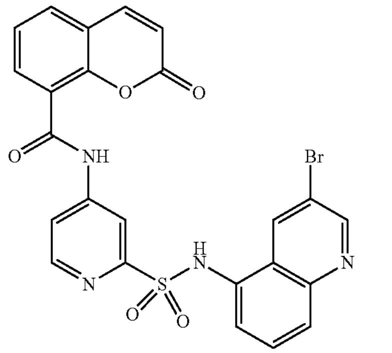 [SMILES: O=C(Nc1ccnc(S(=O)(=O)Nc2cccc3ncc(Br)cc23)c1)c1cccc2ccc(=O)oc12]

In a second aspect, the present application provides a stereoisomer of the 8-(picolinamide)-substituted coumarin compound according to the first aspect, a pharmaceutically acceptable salt of the 8-(picolinamide)-substituted coumarin compound according to the first aspect or a pharmaceutical composition comprising the 8-(picolinamide)-substituted coumarin compound according to the first aspect.

Preferably, the pharmaceutical composition further comprises a pharmaceutically acceptable excipient, such as a vehicle, a diluent, an excipient, a filler, a binder, a wetting agent, a disintegrant, an emulsifier, a co-solvent, a solubilizer, an osmolarity modifier, a surfactant, a coating material, a colorant, a pH modifier, an antioxidant, a bacteriostat or a buffer.

The pharmaceutically acceptable salt of the 8-(picolinamide)-substituted coumarin compound involved in the present application is a salt formed by the 8-(picolinamide)-substituted coumarin compound with an acid selected from: hydrochloric acid, hydrobromic acid, p-toluenesulfonic acid, tartaric acid, maleic acid, lactic acid, methanesulfonic acid, sulfuric acid, phosphoric acid, citric acid, acetic acid or trifluoroacetic acid. Preferably, the salt is selected from hydrochloric acid, hydrobromic acid, p-toluenesulfonic acid or trifluoroacetic acid.

In a third aspect, the present application provides a preparation method for the 8-(picolinamide)-substituted coumarin compound according to the first aspect, and the preparation method comprises:

mixing

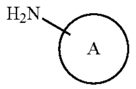

with DIPEA, and then mixing with 4-(2-oxo-2H-chromene-8-carboxamido) pyridine-2-sulfonyl chloride, and reacting to obtain, wherein ring A is defined as in the first aspect;

a reaction formula thereof is as follows:

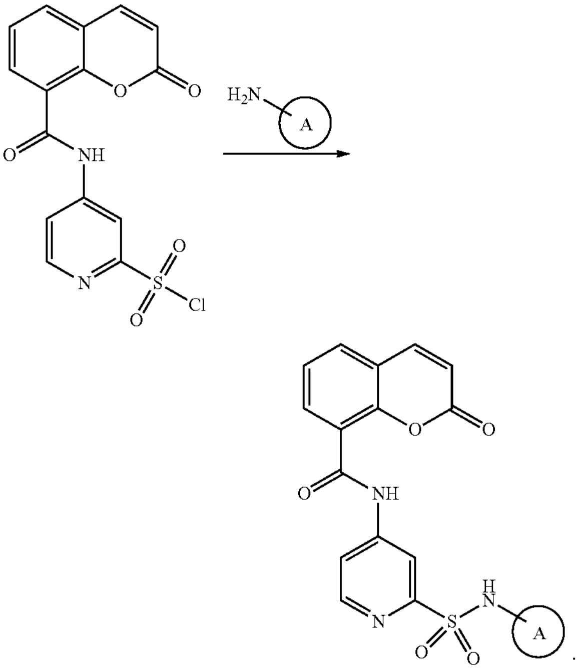

Preferably, a preparation method for the 4-(2-oxo-2H-chromene-8-carboxamido)pyridine-2-sulfonyl chloride comprises the following steps:

(1) mixing 8-bromocoumarin with n-butyllithium, and then mixing with $CO_2$ gas under vacuum, and reacting to obtain coumarin-8-carboxylic acid;

(2) mixing coumarin-8-carboxylic acid with HATU and DIPEA, and then mixing with 4-aminopyridine-2-sulfonic acid, and reacting to obtain 4-(2-oxo-2H-chromene-8-carboxamido) pyridine-2-sulfonic acid; and (3) mixing 4-(2-oxo-2H-chromene-8-carboxamido)pyridine-2-sulfonic acid with thionyl dichloride, and reacting to obtain 4-(2-oxo-2H-chromene-8-carboxamido) pyridine-2-sulfonyl chloride;

a reaction formula thereof is as follows:

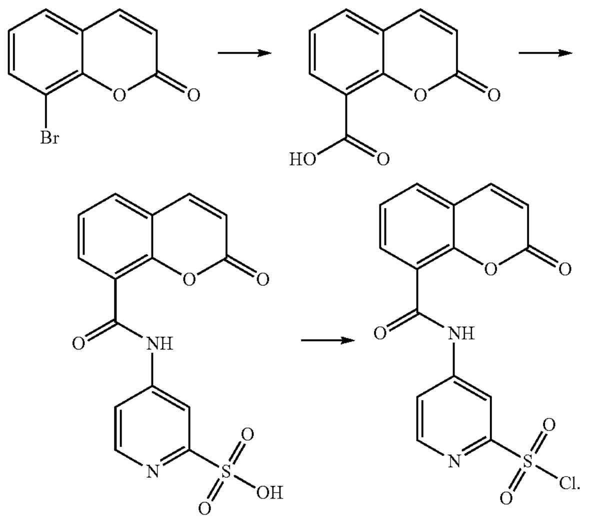

As a preferred technical solution of the present application, the preparation method for 4-(2-oxo-2H-chromene-8-carboxamido)pyridine-2-sulfonyl chloride comprises the following steps:

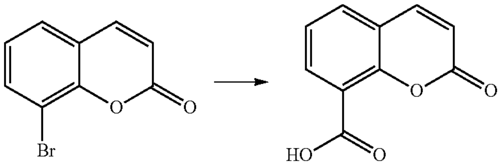 [SMILES: O=c1ccc2cccc(Br)c2o1 ; O=C(O)c1cccc2ccc(=O)oc12]

(1) n-Butyllithium (n-hexane solution) is slowly added to an anhydrous tetrahydrofuran solution of 8-bromocoumarin at −78° C. under nitrogen protection. After being stirred at −78° C. for 3 h, the solution is frozen in a liquid nitrogen bath, then vacuumized, and subsequently introduced with $CO_2$ gas generated by reacting $BaCO_3$ with concentrated sulfuric acid. The mixture is stirred at −78° C. for 2 h and then the reaction is quenched at room temperature with a saturated $NH_4Cl$ aqueous solution. The system is adjusted to pH 5 approximately with hydrochloric acid, extracted with ethyl acetate for three times, and washed with a saturated saline solution for one time, and the combined organic phases are dried with anhydrous sodium sulfate and concentrated. Purification is carried out with silica gel column to obtain coumarin-8-carboxylic acid.

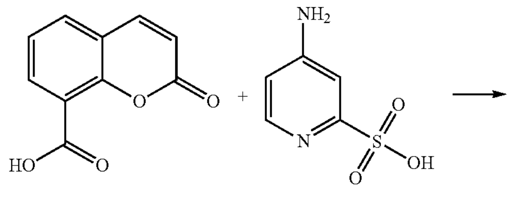

-continued

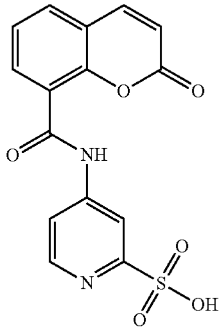

(2) Coumarin-8-carboxylic acid, condensing agent HATU, DIPEA, and ultra-dry dichloromethane are added to a single-necked flask, stirred at room temperature, and then added with a dichloromethane solution of 4-aminopyridine-2-sulfonic acid dropwise. After the dropwise addition, the system is stirred at room temperature for 5 h. The TLC method is carried out to determine the reaction completion. The mixture is added with water, extracted with ethyl acetate for three times, washed with a saturated saline solution, and dried with anhydrous sodium sulfate. Purification is carried out with silica gel column to obtain 4-(2-oxo-2H-chromene-8-carboxamido)pyridine-2-sulfonic acid.

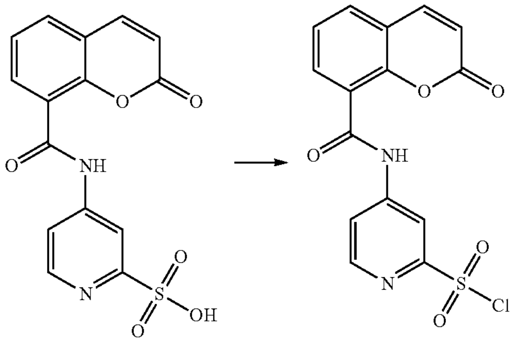 [SMILES: O=C(Nc1ccnc(S(=O)(=O)O)c1)c1cccc2ccc(=O)oc12 ; O=C(Nc1ccnc(S(=O)(=O)Cl)c1)c1cccc2ccc(=O)oc12]

(3) Firstly, thionyl dichloride is introduced into a flask and heated to 60° C. The reaction solution is added with 4-(2-oxo-2H-chromene-8-carboxamido)pyridine-2-sulfonic acid dropwise with stirring, and heated to 60° C. Hydrogen chloride and sulfur dioxide, reaction products, escape as gases through a reflux condenser. After the dropwise addition, the mixture is stirred at 60° C. for another 2 h until no gas escapes. The excess thionyl dichloride is then evaporated off with a vacuum pump. Purification is carried out with silica gel column to obtain 4-(2-oxo-2H-chromene-8-carboxamido) pyridine-2-sulfonyl chloride.

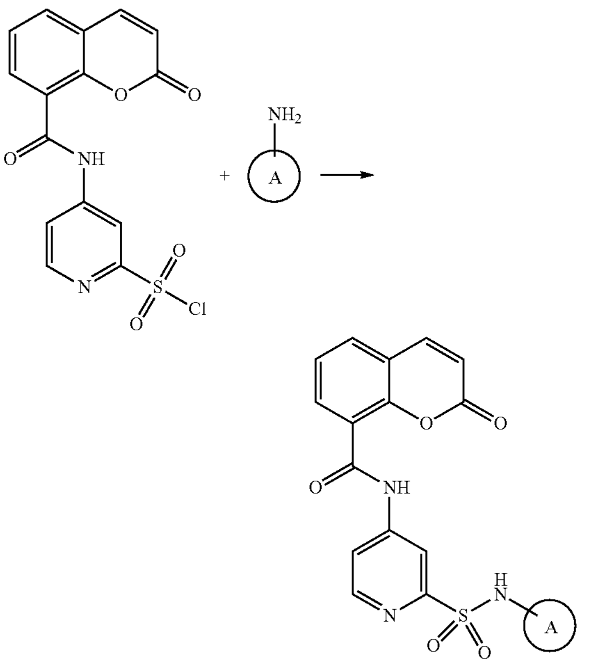

(4) DIPEA is added to an anhydrous tetrahydrofuran solution of various aromatic amines. The mixture is then stirred at room temperature. Subsequently 4-(2-oxo-2H-chromene-8-carboxamido)pyridine-2-sulfonyl chloride is added to the reaction solution. The mixture is stirred at room temperature for 20 min. The TLC method is carried out to determine the reaction completion. Purification is carried out with silica gel column to obtain the product.

In a fourth aspect, the present application provides use of the 8-(picolinamide)-substituted coumarin compound according to the first aspect, or the stereoisomer, the pharmaceutically acceptable salt or the pharmaceutical composition of the 8-(picolinamide)-substituted coumarin compound according to the second aspect, in the preparation of a drug for treating and/or preventing a disease or a disorder associated with excessive SIRT2 activity or SIRT2 overexpression.

Preferably, the disease or the disorder associated with excessive SIRT2 activity or SIRT2 overexpression comprises Parkinson's disease, metabolic disease or tumor.

In a fifth aspect, the present application provides use of the 8-(picolinamide)-substituted coumarin compound according to the first aspect, or the stereoisomer, the pharmaceutically acceptable salt or the pharmaceutical composition of the 8-(picolinamide)-substituted coumarin compound according to the second aspect, in the preparation of a SIRT2 inhibitor.

In a sixth aspect, the present application provides a method for treating and/or preventing a disease or a disorder associated with excessive SIRT2 activity or SIRT2 overexpression, and the method comprises: administering to a subject in need thereof a therapeutically and/or prophylactically effective amount of the 8-(picolinamide)-substituted coumarin compound according to the first aspect, or the stereoisomer, the pharmaceutically acceptable salt or the pharmaceutical composition of the 8-(picolinamide)-substituted coumarin compound according to the second aspect.

Preferably, the disease or the disorder associated with excessive SIRT2 activity or SIRT2 overexpression comprises Parkinson's disease, metabolic disease or tumor.

Aspects and features of the present application are further described below.

The terms and phrases used in the present application have the general meanings known to those skilled in the art; even so, the terms and phrases will be described and explained in more detail in the present application, and where terms and phrases referred to have meanings that are inconsistent with the commonly known meanings, the meanings expressed herein shall prevail. The following are definitions of the terms used in the present application, and these definitions apply to the terms used throughout the specification of the present application, unless otherwise specified. Definitions of the groups of the compounds in the present application are provided below, and they are used consistently throughout the specification and claims unless otherwise defined.

As recited in the present application, the terms "halo", "halogen", "halogen atom" and "halogenate" refer to fluorine, chlorine, bromine or iodine, and in particular fluorine, chlorine or bromine.

As recited in the present application, the term "alkyl" refers to an alkyl group having a specified number of carbon atoms, which may be a linear or branched alkyl group. For example, when "$C_{1-8}$ alkyl" is mentioned, it refers to an alkyl group whose carbon atom number is 1, 2, 3, 4, 5, 6, 7, or 8, and it includes the groups of its subsets such as $C_{1-8}$ alkyl, $C_{1-7}$ alkyl, $C_{2-8}$ alkyl, $C_{2-7}$ alkyl, $C_{2-6}$ alkyl, $C_{3-8}$ alkyl, $C_{3-7}$ alkyl, $C_{3-6}$ alkyl, etc., and preferably the specific groups such as methyl, ethyl, n-propyl, isopropyl, n-butyl, sec-butyl, tert-butyl, pentyl, hexyl, heptyl, and octyl, and further preferably methyl and isopropyl. For example, the "$C_{1-6}$ alkyl" in the "$C_{1-6}$ alkoxy", "$C_{1-6}$ alkylformyl", "$C_{1-6}$ alkoxyformyl" or "$C_{1-6}$ alkyl" refers to an alkyl group whose carbon atom number is 1, 2, 3, 4, 5, or 6, and it includes the groups of its subsets such as $C_{1-5}$ alkyl, $C_{1-4}$ alkyl, $C_{2-6}$ alkyl, $C_{2-5}$ alkyl, $C_{2-4}$ alkyl, $C_{3-6}$ alkyl, $C_{3-5}$ alkyl, $C_{3-4}$ alkyl, etc., and preferably the specific groups such as methyl, ethyl, n-propyl, isopropyl, n-butyl, sec-butyl, tert-butyl, pentyl, and hexyl, and further preferably methyl. For example, the "$C_{1-4}$ alkyl" in the "$C_{1-4}$ alkylcarbonyl" or "$C_{1-4}$ alkoxycarbonyl" refers to an alkyl group whose carbon atom number is 1, 2, 3, or 4, and it includes the groups of its subsets such as $C_{1-4}$ alkyl, $C_{2-4}$ alkyl, etc., and preferably the specific groups such as methyl, ethyl, n-propyl, and isopropyl.

As recited in the present application, the term "cycloalkyl" refers to a circular alkyl group having a specified number of carbon atoms on the ring. For example, when "$C_{3-8}$ cycloalkyl" is mentioned, it refers to a cycloalkyl group whose carbon atom number is 3, 4, 5, 6, 7, or 8, and it includes the groups of its subsets such as $C_{3-7}$ cycloalkyl, $C_{3-4}$ cycloalkyl, $C_{4-6}$ cycloalkyl, etc., and preferably the specific groups such as cyclopropyl, cyclobutyl, cyclopentyl, cyclohexyl, cycloheptyl, and cyclooctyl, and further preferably cyclopropyl, cyclopentyl and cyclohexyl. For example, the "$C_{3-6}$ cycloalkyl" refers to a cycloalkyl group whose carbon atom number is 3, 4, 5, or 6, and it includes the groups of its subsets such as $C_{3-6}$ cycloalkyl, $C_{3-5}$ cycloalkyl, $C_{4-5}$ cycloalkyl, etc., and preferably the specific groups such as cyclopropyl, cyclobutyl, cyclopentyl, cyclohexyl, and cycloheptyl, and further preferably cyclopropyl, cyclopentyl and cyclohexyl.

As recited in the present application, the term "aromatic heterocyclic group" refers to a heterocyclic aromatic system having one to four heteroatoms, and the heteroatoms include nitrogen, oxygen and sulfur. As recited in the present application, the term "5-14-membered aromatic heterocyclic group" refers to a heterocyclic aromatic system having five to fourteen atoms on the ring. A specific example includes an aryl group containing one carbon atom and four heteroatoms selected from nitrogen, oxygen and sulfur, and preferably the specific groups such as tetrazolyl; an aryl group containing two carbon atoms and three heteroatoms selected from nitrogen, oxygen and sulfur, and preferably the specific groups such as 1,2,3-triazolyl, 1,2,4-triazolyl, oxadiazolyl, and thiadiazolyl; an aryl group containing three carbon atoms and two heteroatoms selected from nitrogen, oxygen and sulfur, and preferably the specific groups such as imidazolyl, pyrazolyl, oxazolyl, isoxazolyl, thiazolyl, and isothiazolyl; an aryl group containing four carbon atoms and one to two heteroatoms selected from nitrogen, oxygen and sulfur, and preferably the specific groups such as pyrrolyl, furanyl, thiophenyl, pyridazinyl, pyrimidinyl, and pyrazinyl; an aryl group containing five carbon atoms and one heteroatom selected from nitrogen, oxygen and sulfur, and preferably the specific groups such as pyridinyl, and preferably pyridinyl; an aryl group containing six carbon atoms and three heteroatoms selected from nitrogen, oxygen and sulfur, and preferably the specific groups such as benzotriazolyl; an aryl group containing seven carbon atoms and two heteroatoms selected from nitrogen, oxygen and sulfur, and preferably the specific groups such as benzimidazolyl, and benzopyrazolyl; an aryl group containing eight carbon atoms and one to two heteroatoms selected from nitrogen, oxygen and sulfur, and preferably the specific groups such as indolyl, benzofuranyl, benzothienyl, benzopyrazinyl, benzopyrimidinyl, and benzpyridazinyl; an aryl group containing nine carbon atoms and one heteroatom selected from nitrogen, oxygen and sulfur, and preferably the specific groups such as quinolinyl, and isoquinolinyl.

As recited in the present application, the term "effective amount" means a dosage that achieves the treatment and/or prevention of a disease or a disorder described in the present application for a subject.

As recited in the present application, the term "pharmaceutical composition" may also refer to a "composition", which can be used in a subject, especially a mammal, to achieve the treatment and/or prevention of a disease or disorder described in the present application.

As recited in the present application, the term "subject" may refer to a patient or other animal, in particular a mammal, such as a human, a dog, a monkey, a cow, a horse, etc., which receives a compound, a pharmaceutical salt, or a pharmaceutical composition thereof, as recited in the present application, to treat and/or prevent a disease or disorder described in the present application.

As recited in the present application, the term "disease and/or disorder" refers to a physical condition of the subject which is associated with the disease and/or disorder described herein. For example, the disease and/or disorder recited herein may refer to either a physical condition, such as a physical condition of Parkinson's disease, or a disease condition, such as a disease condition manifesting itself as Parkinson's disease. No distinction is made herein between the physical condition and the disease condition, or the two may refer to each other, and for example, "Parkinson's disease" and "Parkinson's disorder" may be used interchangeably.

As recited in the present application, the term "pharmaceutically acceptable", for example, when describing a "pharmaceutically acceptable salt", indicates that the salt is not only physiologically acceptable to the subject, but also refers to a synthetic substance that is pharmaceutically useful, for example, a salt formed as an intermediate for enantioseparation; although such intermediate salt cannot be directly administered to the subject, it plays a role in obtaining the final product of the present application.

Another aspect of the present application relates to a pharmaceutical composition wherein the compound of the present application is an active ingredient. The pharmaceutical composition can be prepared according to the known method in the art. The compound of the present application can be combined with one or more pharmaceutically acceptable solid or liquid excipients and/or auxiliary substances to be prepared into any dosage form suitable for human or animal. A content of the compound of the present application is typically 0.1-95% by weight in the pharmaceutical composition thereof.

The compound of the present application or the pharmaceutical composition containing the same may be administered in a unit dose form, and the route of administration may be intestinal or non-intestinal administration, and for example, oral, intravenous injection, intramuscular injection, subcutaneous injection, nasal cavity, oral mucosa, eye, lung and respiratory tracts, skin, vagina, rectum, etc.

The dosage form may be a liquid dosage form, a solid dosage form, or a semi-solid dosage form. The liquid dosage form can be solutions (including true solutions and colloidal solutions), emulsions (including o/w-type, w/o-type and compound emulsions), suspensions, injections (including aqueous injections, powdered injections and infusions), eye drops, nasal drops, lotions and liniments, etc.; the solid dosage form can be tablets (including ordinary tablets, enteric-coated tablets, lozenges, dispersible tablets, chewable tablets, effervescent tablets, and orally disintegrating tablets), capsules (including hard capsules , soft capsules, and enteric capsules), granules, pulvis, micro-pills, drops, suppositories, films, patches, aerosols/powder inhalation, sprays, etc.; the semi-solid dosage form can be ointments, gels, pastes, etc.

The compound of the present application can be prepared into ordinary formulations, or into sustained-release formulations, controlled-release formulations, targeted formulations and particulate drug delivery systems.

In order to prepare the compound of the present application into tablets, a wide range of excipients known in the art can be used, including a diluent, a binder, a wetting agent, a disintegrant, a lubricant, and a co-solvent. The diluent may be starch, dextrin, sucrose, glucose, lactose, mannitol, sorbitol, xylitol, microcrystalline cellulose, calcium sulfate, calcium hydrogen phosphate, calcium carbonate, etc.; the wetting agent may be water, ethanol, isopropanol, etc.; the binder may be starch slurry, dextrin, molasses, honey, dextrose solution, microcrystalline cellulose, gum arabic slurry, gelatin slurry, sodium carboxymethylcellulose, methyl cellulose, hydroxypropyl methyl cellulose, ethyl cellulose, acrylic resin, carbomer, polyvinylpyrrolidone, polyethylene glycol, etc.; the disintegrant may be dry starch, microcrystalline cellulose, low-substituted hydroxypropyl cellulose, crosslinked polyvinylpyrrolidone, crosslinked sodium carboxymethylcellulose, sodium carboxymethylstarch, sodium bicarbonate and citric acid, polyoxyethylene sorbitol fatty acid esters, sodium dodecylsulphonate, etc.; the lubricant and the co-solvent can be talc, silica, stearate, tartaric acid, liquid paraffin, polyethylene glycol, etc.

The tablets may further be prepared into coated tablets, such as sugar-coated tablets, film-coated tablets, enteric-coated tablets, or bilayer tablets and multilayer tablets.

In order to prepare the administration unit into capsules, the compound of the present application (the active ingredient) can be mixed with a diluent and a co-solvent, and the mixture can be directly introduced into hard or soft capsules. Also, the compound of the present application (the active ingredient) can be firstly prepared into granules or micropills with the diluent, binder and disintegrant and then introduced into hard or soft capsules. The diluent, binder, wetting agent, disintegrant, co-solvent species used to prepare tablets of the compound of the present application can also be used to prepare capsules of the compound of the present application.

In order to prepare the compound of the present application into injections, the water, ethanol, isopropanol, propylene glycol or mixtures thereof may be used as the solvent and added with appropriate amounts of solubilizer, co-solvent, pH modifier, and osmolarity modifier commonly used in the art. The solubilizer or co-solvent can be poloxamer, lecithin, hydroxypropyl-β-cyclodextrin, etc.; the pH modifier can be phosphate, acetate, hydrochloric acid, sodium hydroxide, etc.; the osmolarity modifier can be sodium chloride, mannitol, glucose, phosphate, acetate, etc. In a case where a lyophilized powder injection is prepared, the mannitol and glucose may also be added as a support agent.

In addition, the pharmaceutical preparation may also be added with a colorant, a preservative, a flavor, a spice, a flavoring agent or other additives, if needed.

For the purpose of administration and to enhance the therapeutic effect, the drug or pharmaceutical composition of the present application can be administered in any well-known ways.

The dosage of the pharmaceutical composition of the compound of the present application can vary widely depending on the nature and severity of the disease to be prevented or treated, the individual condition of the patient or animal, the route of administration, the dosage form, etc. In general, the suitable daily dosage of the compound involved in the present application ranges from 0.001 mg to 150 mg per kg of body weight, preferably from 0.1 mg to 100 mg per kg of body weight, more preferably from 1 mg to 60 mg per kg of body weight, and most preferably from 2 mg to 30 mg per kg of body weight. The above dosages may be administered as a single dosage unit or divided into several dosage units, depending on the clinical experience of the doctor and the dosing regimen including other therapeutic means.

The compound or composition of the present application may be administrated alone or in conjunction with other therapeutic or symptomatic drugs. When the compound of the present application has a synergistic effect with other therapeutic drugs, its dosage should be adjusted accordingly.

Compared with the prior art, the present application has the following beneficial effects.

The 8-(picolinamide)-substituted coumarin compound involved in the present application is a new compound structure and has an in vitro SIRT2 inhibitory activity of 50% or more, wherein eighteen of the compounds have an in vitro SIRT2 inhibitory activity ($IC_{50}$) at micromolar level, and in particular eleven of the compounds have $IC_{50}$ values at $10^{-7}$ mol/L level, and four of the compounds have $IC_{50}$ values at $10^{-8}$ mol/L level, showing good SIRT2 inhibitory activity and significant protective effect on neuroblastoma cells. Hence, the 8-(picolinamide)-substituted coumarin compound can be widely used in the preparation of a drug for treating and/or preventing a disease or a disorder associated with excessive SIRT2 activity or SIRT2 overexpression or in the preparation of a drug for treating and/or preventing Parkinson's disease, metabolic disease, or tumor.

BRIEF DESCRIPTION OF DRAWINGS

FIG. 1 is a statistical diagram showing the protective effects of 8-(picolinamide)-substituted coumarin compounds involved in the present application against SH-SY5Y cell damage in Testing Example 3.

DETAILED DESCRIPTION

The technical solutions of the present application are described in detail below through specific embodiments. It should be apparent to those skilled in the art that the examples are merely used for a better understanding of the present application and should not be regarded as a specific limitation on the present application.

For all of the following examples or preparation examples, standard operations and purification methods known to those skilled in the art may be used. Unless otherwise indicated, the temperature is expressed in ° C. (degrees Celsius) and the compound structure is determined by nuclear magnetic resonance spectroscopy (NMR) and/or mass spectroscopy (MS).

For all of the following examples or preparation examples, the compound structure is determined by proton nuclear magnetic resonance spectroscopy ($^1$H NMR) and/or mass spectroscopy (MS). The shift (δ) in $^1$H NMR is expressed in parts per million (ppm). The NMR spectra are determined with a Mercury-300 or Mercury-400 NMR instrument, with deuterated chloroform ($CDCl_3$) or deuterated dimethylsulfoxide (DMSO-d6) as solvent, and with tetramethylsilane (TMS) or 3-(trimethylsilyl)propionic acid-d4 sodium salt (TSM) as internal reference.

The electronic balance of Yanaco LY-300 (Japan) is used.

The 200-300 mesh or 300-400 mesh silica gel is used as carrier for column chromatography.

Anhydrous solvents are treated by standard methods. The other reagents are analytically pure and commercially available.

For the reagents,

HATU is 2-(7-Azabenzotriazol-1-yl)-N,N,N′,N′-tetramethyluronium hexafluor-ophosphat.

DIPEA is N,N-diisopropylethylamine.

DMF is N,N-dimethylformamide.

The sources of raw materials involved in the preparation examples and examples are as follows:

8-bromocoumarin is purchased from Shanghai Aladdin Biochemical Technology Co., Ltd. (CAS: 33491-30-4);

4-aminopyridine-2-sulfonic acid is purchased from SYNCHEM-OHG (CAS: 900804-14-0);

4-chloroaniline, 3-chloroaniline, 2-chloroaniline, 4-methylaniline, 3-nitroaniline, 2-cyanobenzenamine, 4-fluoroaniline, 4-methylsulfonylaniline, 4-trifluoromethylaniline, 4-phenylaniline, 4-hydroxyaniline, 4-methoxyaniline, 3,4-fluoroaniline, 3-bromo-4-chloroaniline, 7-bromo-1-naphthylamine, 3-chloro-1-naphthylamine, 5-aminoquinoline, and 3-bromo-5-aminoquinoline are purchased from Shanghai Maclean Biochemical Technology Co., Ltd., Sigma-Aldrich (Shanghai) Trading Co., Ltd., Beijing J&K Scientific Ltd., Meryer (Shanghai) Biochemical Technology Co., Ltd., Alfa Aesar (China) Chemical Co., Ltd., Beijing Ouhe Technologh Co., Ltd., Shanghai Aladdin Biochemical Technology Co., Ltd., Beijing Solarbio Science & Technology Co., Ltd., and Beijing InnoChem Science & Technology Co., Ltd., respectively.

Preparation Example 1

In this preparation example, intermediate 4 shown in the formula below is prepared by the following synthesis route:

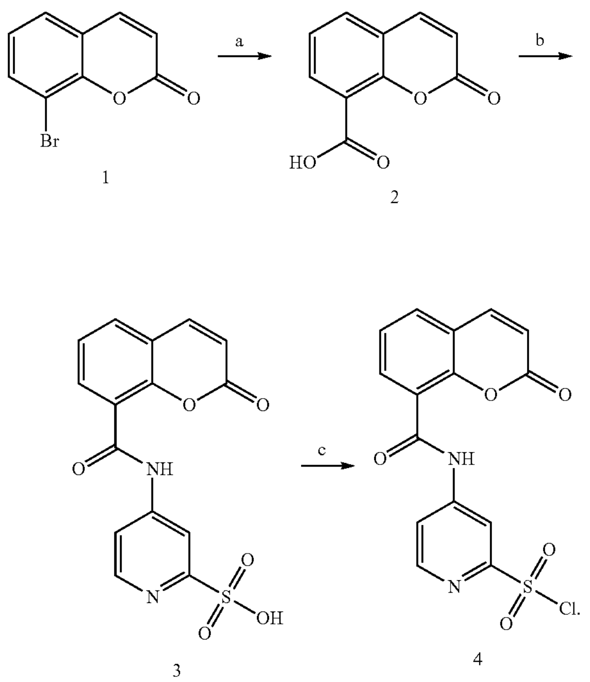

(1) n-Butyllithium (1.60 M n-hexane solution) (14.00 mL, 22.33 mmol) was slowly added to an anhydrous tetrahydrofuran solution (30 mL) of 8-bromocoumarin (5.00 g, 22.33 mmol) at −78° C. under nitrogen protection. After being stirred at −78° C. for 3 h, the solution was frozen in a liquid nitrogen bath, then vacuumized, and subsequently introduced with $CO_2$ gas generated by reacting $BaCO_3$ (5.29 g, 26.80 mmol) with concentrated sulfuric acid (1.43 mL, 26.80 mmol). The mixture was stirred at −78° C. for 2 h, and then the reaction was quenched at 20° C. with a saturated $NH_4Cl$ aqueous solution. The system was adjusted to pH=5 with hydrochloric acid, extracted with ethyl acetate for three times (15 mL×3), and washed with a saturated saline solution for one time, and the combined organic phases were dried with anhydrous sodium sulfate and concentrated. Purification was carried out with silica gel column to obtain the product coumarin-8-carboxylic acid (1.61 g, 38% yield).

(2) Coumarin-8-carboxylic acid (1.60 g, 8.42 mmol), condensing agent HATU (3.20 g, 8.42 mmol), DIPEA (2.93 mL, 16.84 mmol), and ultra-dry dichloromethane (15 mL) were added to a single-necked flask, stirred at 20° C. for 30 min, and then added with a dichloromethane solution (5 mL) of 4-aminopyridine-2-sulfonic acid (1.33 g, 7.65 mmol) dropwise. After the dropwise addition, the system was stirred at 20° C. for 5 h. The TLC method was carried out to determine the reaction completion. The mixture was added with water, extracted with ethyl acetate for three times (15 mL×3), washed with a saturated saline solution, and dried with anhydrous sodium sulfate. Purification was carried out with silica gel column to obtain the product 4-(2-oxo-2H-chromene-8-carboxamido)pyridine-2-sulfonic acid (1.61 g, 61% yield).

(3) Firstly, thionyl dichloride (5 mL) was introduced into a flask and heated to 60° C. The reaction solution was added with 4-(2-oxo-2H-chromene-8-carboxamido) pyridine-2-sulfonic acid (1.60 g, 4.62 mmol) dropwise over 3 hours while being stirred, and heated to 60° C. Hydrogen chloride and sulfur dioxide, reaction products, escaped as gases through a reflux condenser. After the dropwise addition, the mixture was stirred at 60° C. for another 2 h until no gas escaped. The excess thionyl dichloride was then evaporated off with a vacuum pump. Purification was carried out with silica gel column to obtain the product 4-(2-oxo-2H-chromene-8-carboxamido) pyridine-2-sulfonyl chloride (0.59 g, 35% yield).

Example 1

In this example, Compound 1, N-(2-(N-(4-chlorophenyl) aminosulfonyl)-pyridin-4-yl)-2-oxo-2H-chromene-8-amide, is prepared, which has a structure shown below:

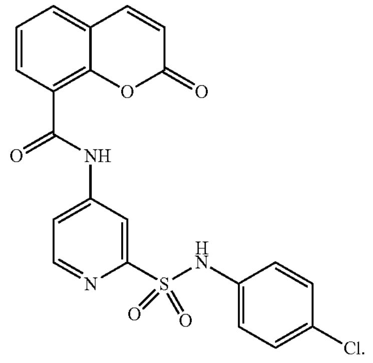 [SMILES: O=C(Nc1ccnc(S(=O)(=O)Nc2ccc(Cl)cc2)c1)c1cccc2ccc(=O)oc12]

An anhydrous tetrahydrofuran solution (10 mL) of 4-chloroaniline (0.17 g, 1.37 mmol, CAS: 106-47-8) was added with DIPEA (0.48 mL, 2.74 mmol). Then, the mixture was stirred at 20° C. for 10 min. Subsequently, 4-(2-oxo-2H-chromene-8-carboxamido)pyridine-2-sulfonyl chloride (0.50 g, 1.37 mmol) was added to the reaction solution. The mixture was stirred at 20° C. for 20 min. The TLC method was carried out to determine the reaction completion. Purification was carried out with silica gel column to obtain the product (0.21 g, 33% yield). The product was characterized as follows:

$^1H$ NMR (400 MHz, $CDCl_3$): δ 8.54 (d, J=4.4 Hz, 1H), 7.52-7.79 (m, 4H), 7.10-7.41 (m, 5H), 6.52 (m, 1H), 5.97 (m, 1H).

HR-MS (ESI): $[M+H]^+$ $C_{21}H_{15}ClN_3O_5S$, calculated value 456.0421, measured value 456.0454.

Example 2

In this example, Compound 2, N-(2-(N-(3-chlorophenyl) aminosulfonyl)-pyridin-4-yl)-2-oxo-2H-chromene-8-amide, is prepared, which has a structure shown below:

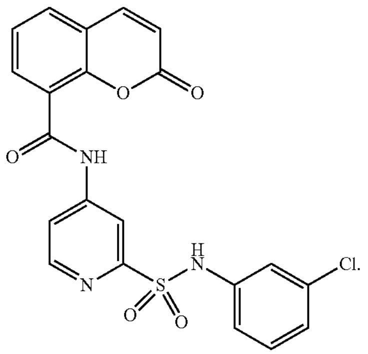 [SMILES: O=C(Nc1ccnc(S(=O)(=O)Nc2cccc(Cl)c2)c1)c1cccc2ccc(=O)oc12]

The preparation method was carried out with reference to Example 1, wherein 4-chloroaniline was replaced with 3-chloroaniline, to obtain a white solid (0.16 g, 26% yield). The product was characterized as follows:

$^1H$ NMR (400 MHz, $CDCl_3$): 8.53 (d, J=5.4 Hz, 1H), 7.52-7.79 (m, 4H), 7.10-7.38 (m, 5H), 6.52 (m, 1H), 5.97 (m, 1H).

HR-MS (ESI): $[M+H]^+$ $C_{21}H_{15}ClN_3O_5S$, calculated value 456.0421, measured value 456.0434.

Example 3

In this example, Compound 3, N-(2-(N-(2-chlorophenyl) aminosulfonyl)-pyridin-4-yl)-2-oxo-2H-chromene-8-amide, is prepared, which has a structure shown below:

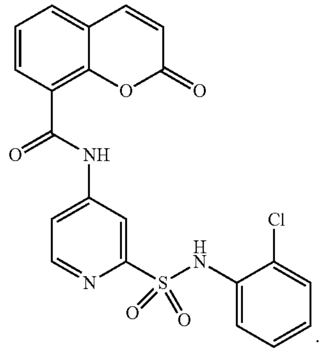

The preparation method was carried out with reference to Example 1, wherein 4-chloroaniline was replaced with 2-chloroaniline, to obtain a white solid (0.26 g, 42% yield). The product was characterized as follows:

$^1H$ NMR (400 MHz, $CDCl_3$): δ 8.54 (d, J=4.4 Hz, 1H), 7.52-7.79 (m, 4H), 7.15-7.38 (m, 5H), 6.52 (m, 1H), 5.97 (m, 1H).

HR-MS (ESI): $[M+H]^+$ $C_{21}H_{15}ClN_3O_5S$, calculated value 456.0421, measured value 456.0414.

Example 4

In this example, Compound 4, N-(2-(N-(4-methylphenyl) aminosulfonyl)-pyridin-4-yl)-2-oxo-2H-chromene-8-amide, is prepared, which has a structure shown below:

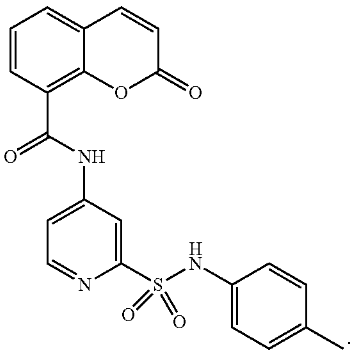 [SMILES: Cc1ccc(NS(=O)(=O)c2cc(NC(=O)c3cccc4ccc(=O)oc34)ccn2)cc1]

The preparation method was carried out with reference to Example 1, wherein 4-chloroaniline was replaced with 4-methylaniline, to obtain a white solid (1.97 g, 33% yield). The product was characterized as follows:

$^1H$ NMR (400 MHz, $CDCl_3$): δ 8.54 (d, J=4.4 Hz, 1H), 7.53-7.78 (m, 4H), 7.12-7.49 (m, 5H), 6.52 (m, 1H), 5.97 (m, 1H), 2.34 (s, 3H).

HR-MS (ESI): $[M+H]^+$ $C_{22}H_{18}N_3O_5S$, calculated value 436.0967, measured value 436.0945.

Example 5

In this example, Compound 5, N-(2-(N-(3-nitrophenyl) aminosulfonyl)-pyridin-4-yl)-2-oxo-2H-chromene-8-amide, is prepared, which has a structure shown below:

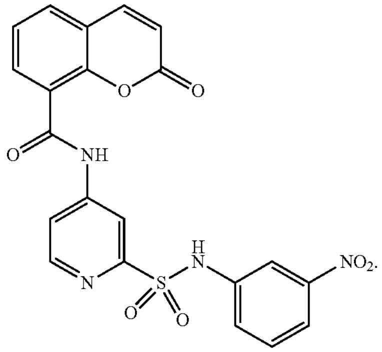 [SMILES: O=C(Nc1ccnc(S(=O)(=O)Nc2cccc([N+](=O)[O-])c2)c1)c1cccc2ccc(=O)oc12]

The preparation method was carried out with reference to Example 1, wherein 4-chloroaniline was replaced with 3-nitroaniline, to obtain a white solid (0.23 g, 36% yield). The product was characterized as follows:

$^1H$ NMR (400 MHz, $CDCl_3$): δ 8.53 (d, J=5.4 Hz, 1H), 7.50-7.77 (m, 4H), 7.10-7.36 (m, 5H), 6.54 (m, 1H), 5.92 (m, 1H).

HR-MS (ESI): $[M+H]^+$ $C_{21}$ $H_{15}N_4O_7S$, calculated value 467.0661, measured value 467.0646.

Example 6

In this example, Compound 6, N-(2-(N-(2-cyanophenyl) aminosulfonyl)-pyridin-4-yl)-2-oxo-2H-chromene-8-amide, is prepared, which has a structure shown below:

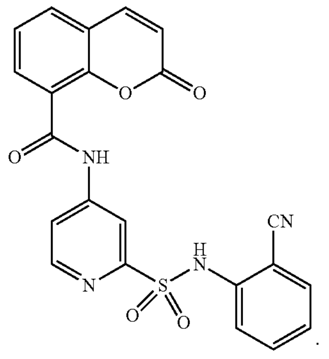 [SMILES: N#Cc1ccccc1NS(=O)(=O)c1cc(NC(=O)c2cccc3ccc(=O)oc23)ccn1]

The preparation method was carried out with reference to Example 1, wherein 4-chloroaniline was replaced with 2-cyanoaniline, to obtain a white solid (0.153 g, 25% yield). The product was characterized as follows:

$^{1}H$ NMR (400 MHz, $CDCl_3$): δ 8.53 (d, J=5.2 Hz, 1H), 7.52-7.75 (m, 4H), 7.10-7.42 (m, 5H), 6.52 (m, 1H), 5.97 (m, 1H).

HR-MS (ESI): $[M+H]^+$ $C_{22}H_{15}N_4O_5S$, calculated value 447.0763, measured value 447.0742.

Example 7

In this example, Compound 7, N-(2-(N-(4-fluorophenyl) aminosulfonyl)-pyridin-4-yl)-2-oxo-2H-chromene-8-amide, is prepared, which has a structure shown below:

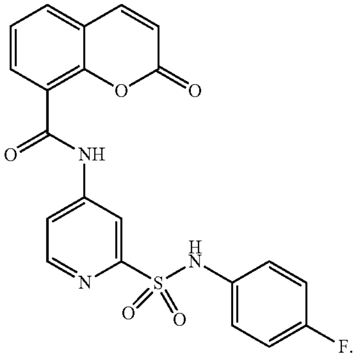 [SMILES: O=C(Nc1ccnc(S(=O)(=O)Nc2ccc(F)cc2)c1)c1cccc2ccc(=O)oc12]

The preparation method was carried out with reference to Example 1, wherein 4-chloroaniline was replaced with 4-fluoroaniline, to obtain a white solid (0.17 g, 29% yield). The product was characterized as follows:

$^{1}H$ NMR (400 MHz, $CDCl_3$): δ 8.62 (d, J=4.7 Hz, 1H), 7.52-7.79 (m, 4H), 7.15-7.42 (m, 5H), 6.52 (m, 1H), 5.97 (m, 1H).

HR-MS (ESI): $[M+H]^+$ $C_{21}H_{15}FN_3O_5S$, calculated value 440.0716, measured value 440.0740.

Example 8

In this example, Compound 8, N-(2-(N-(4-methylsulfonylphenyl)aminosulfonyl)-pyridin-4-yl)-2-oxo-2H-chromene-8-amide, is prepared, which has a structure shown below:

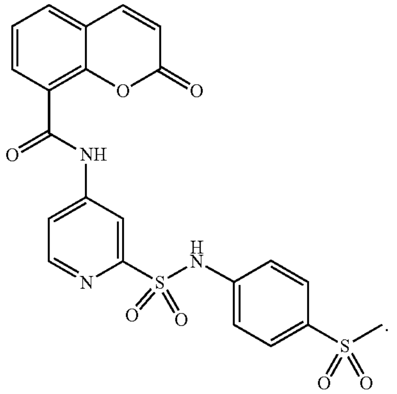 [SMILES: CS(=O)(=O)c1ccc(NS(=O)(=O)c2cc(NC(=O)c3cccc4ccc(=O)oc34)ccn2)cc1]

The preparation method was carried out with reference to Example 1, wherein 4-chloroaniline was replaced with 4-methylsulfonylaniline, to obtain a white solid (0.27 g, 39% yield). The product was characterized as follows:

$^{1}H$ NMR (400 MHz, $CDCl_3$): δ 8.62 (d, J=4.7 Hz, 1H), 7.52-7.77 (m, 4H), 7.11-7.38 (m, 5H), 6.51 (m, 1H), 5.93 (m, 1H), 3.32 (s, 3H).

HR-MS (ESI): $[M+H]^+$ $C_{22}H_{18}N_3O_7S_2$, calculated value 500.0586, measured value 500.0594.

Example 9

In this example, Compound 9, N-(2-(N-(4-trifluoromethylphenyl)aminosulfonyl)-pyridin-4-yl)-2-oxo-2H-chromene-8-amide, is prepared, which has a structure shown below:

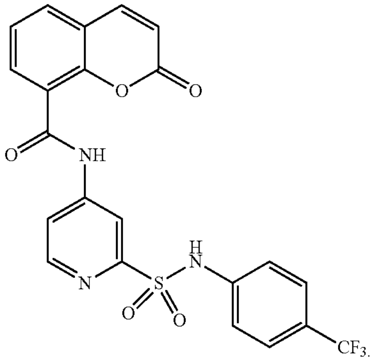 [SMILES: O=C(Nc1ccnc(S(=O)(=O)Nc2ccc(C(F)(F)F)cc2)c1)c1cccc2ccc(=O)oc12]

The preparation method was carried out with reference to Example 1, wherein 4-chloroaniline was replaced with 4-trifluoromethylaniline, to obtain a white solid (0.26 g, 39% yield). The product was characterized as follows:

$^{1}H$ NMR (400 MHz, $CDCl_3$): δ 8.62 (d, J=4.7 Hz, 1H), 7.58-7.79 (m, 4H), 7.11-7.49 (m, 5H), 6.52 (m, 1H), 5.76 (m, 1H).

HR-MS (ESI): $[M+H]^+$ $C_{22}H_{15}F_3N_3O_5S$, calculated value 490.0685, measured value 490.0683.

Example 10

In this example, Compound 10, N-(2-(N-(4-phenylphenyl)aminosulfonyl)-pyridin-4-yl)-2-oxo-2H-chromene-8-amide, is prepared, which has a structure shown below:

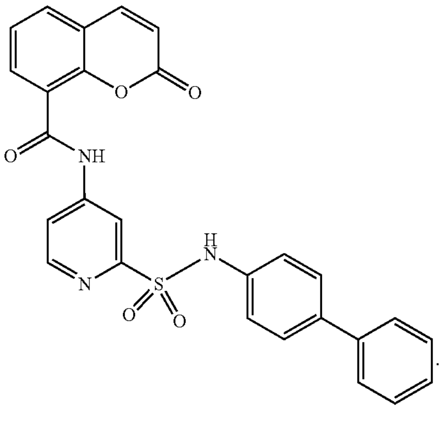 [SMILES: O=C(Nc1ccnc(S(=O)(=O)Nc2ccc(-c3ccccc3)cc2)c1)c1cccc2ccc(=O)oc12]

The preparation method was carried out with reference to Example 1, wherein 4-chloroaniline was replaced with 4-phenylaniline, to obtain a white solid (0.28 g, 41% yield). The product was characterized as follows:

$^1$H NMR (400 MHz, $CDCl_3$): δ 8.62 (d, J=4.7 Hz, 1H), 8.09-8.23 (m, 2H), 7.55-7.89 (m, 10H), 6.52-6.78 (m, 2H), 5.76-6.12 (m, 2H).

HR-MS (ESI): $[M+H]^+$ $C_{27}H_{20}N_3O_5S$, calculated value 498.1124, measured value 498.1145.

Example 11

In this example, Compound 11, N-(2-(N-(4-hydroxyphenyl)aminosulfonyl)-pyridin-4-yl)-2-oxo-2H-chromene-8-amide, is prepared, which has a structure shown below:

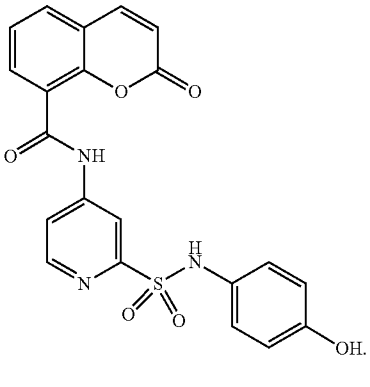 [SMILES: O=C(Nc1ccnc(S(=O)(=O)Nc2ccc(O)cc2)c1)c1cccc2ccc(=O)oc12]

The preparation method was carried out with reference to Example 1, wherein 4-chloroaniline was replaced with 4-hydroxyaniline, to obtain a white solid (0.12 g, 21% yield). The product was characterized as follows:

$^1$H NMR (400 MHz, $CDCl_3$): δ 8.72 (d, J=4.9 Hz, 1H), 7.62-7.77 (m, 4H), 7.12-7.56 (m, 5H), 6.42 (m, 1H), 5.66 (m, 1H), 5.45 (s, 1H).

HR-MS (ESI): $[M+H]^+$ $C_{21}H_{16}N_3O_6S$, calculated value 438.0760, measured value 438.0788.

Example 12

In this example, Compound 12, N-(2-(N-(4-methoxylphenyl)aminosulfonyl)-pyridin-4-yl)-2-oxo-2H-chromene-8-amide, is prepared, which has a structure shown below:

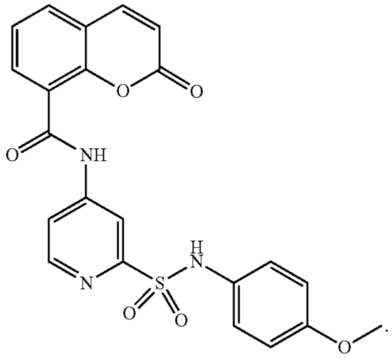 [SMILES: COc1ccc(NS(=O)(=O)c2cc(NC(=O)c3cccc4ccc(=O)oc34)ccn2)cc1]

The preparation method was carried out with reference to Example 1, wherein 4-chloroaniline was replaced with 4-methoxylaniline, to obtain a white solid (0.16 g, 26% yield). The product was characterized as follows:

$^1$H NMR (400 MHz, $CDCl_3$): δ 8.72 (d, J=4.5 Hz, 1H), 7.62-7.76 (m, 4H), 7.12-7.66 (m, 5H), 6.42 (m, 1H), 5.66 (m, 1H), 3.83 (s, 3H).

HR-MS (ESI): $[M+H]^+$ $C_{22}H_{18}N_3O_6S$, calculated value 452.0916, measured value 452.0933.

Example 13

In this example, Compound 13, N-(2-(N-(3,4-difluorophenyl)aminosulfonyl)-pyridin-4-yl)-2-oxo-2H-chromene-8-amide, is prepared, which has a structure shown below:

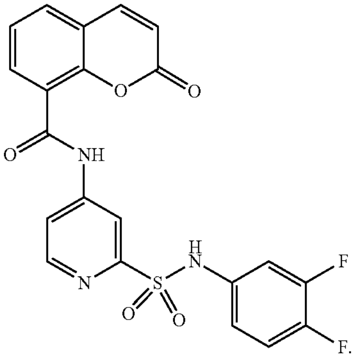 [SMILES: O=C(Nc1ccnc(S(=O)(=O)Nc2ccc(F)c(F)c2)c1)c1cccc2ccc(=O)oc12]

The preparation method was carried out with reference to Example 1, wherein 4-chloroaniline was replaced with 3,4-difluoroaniline, to obtain a white solid (0.22 g, 36% yield). The product was characterized as follows:

$^1$H NMR (400 MHz, $CDCl_3$): δ 8.62 (d, J=5.7 Hz, 1H), 7.57-7.77 (m, 4H), 7.13-7.49 (m, 4H), 6.62 (m, 1H), 5.93 (m, 1H).

HR-MS (ESI): $[M+H]^+$ $C_{21}H_{14}F_1N_3O_5S$, calculated value 458.0622, measured value 458.0636.

Example 14

In this example, Compound 14, N-(2-(N-(3-bromo-4-chlorophenyl)aminosulfonyl)-pyridin-4-yl)-2-oxo-2H-chromene-8-amide, is prepared, which has a structure shown below:

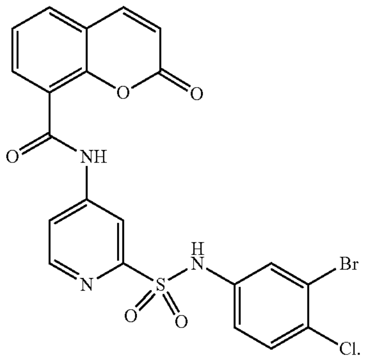 [SMILES: O=C(Nc1ccnc(S(=O)(=O)Nc2ccc(Cl)c(Br)c2)c1)c1cccc2ccc(=O)oc12]

The preparation method was carried out with reference to Example 1, wherein 4-chloroaniline was replaced with 3-bromo-4-chloroaniline, to obtain a white solid (0.23 g, 32% yield). The product was characterized as follows:

$^1$H NMR (400 MHz, $CDCl_3$): δ 8.62 (d, J=5.7 Hz, 1H), 7.53-7.78 (m, 4H), 7.15-7.41 (m, 4H), 6.62 (m, 1H), 5.93 (m, 1H).

HR-MS (ESI): $[M+H]^+$ $C_{21}H_{14}BrClN_3O_5S$, calculated value 533.9526, measured value 533.9554.

Example 15

In this example, Compound 15, N-(2-(N-(7-bromonaphth-1-yl)aminosulfonyl)-pyridin-4-yl)-2-oxo-2H-chromene-8-amide, is prepared, which has a structure shown below:

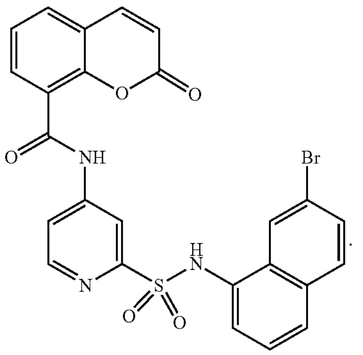

The preparation method was carried out with reference to Example 1, wherein 4-chloroaniline was replaced with 7-bromo-1-naphthylamine, to obtain a white solid (0.19 g, 26% yield). The product was characterized as follows:

$^1$H NMR (400 MHz, $CDCl_3$): δ 8.56 (d, J=54 Hz, 1H), 8.10-8.13 (m, 3H), 7.52-7.81 (m, 4H), 7.02-7.45 (m, 4H), 6.67-6.89 (m, 2H).

HR-MS (ESI): $[M+H]^+$ $C_{25}H_{17}BrN_3O_5S$, calculated value 550.0072, measured value 550.0098.

Example 16

In this example, Compound 16, N-(2-(N-(3-chloronaphth-1-yl)aminosulfonyl)-pyridin-4-yl)-2-oxo-2H-chromene-8-amide, is prepared, which has a structure shown below:

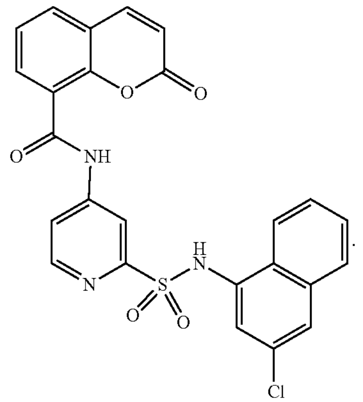 [SMILES: O=C(Nc1ccnc(S(=O)(=O)Nc2cc(Cl)cc3ccccc23)c1)c1cccc2ccc(=O)oc12]

The preparation method was carried out with reference to Example 1, wherein 4-chloroaniline was replaced with 3-chloro-1-naphthylamine, to obtain a white solid (0.20 g, 29% yield). The product was characterized as follows:

$^1$H NMR (400 MHz, $CDCl_1$): δ 8.56 (d, J=54 Hz, 1H), 8.11-8.15 (m, 3H), 7.55-7.87 (m, 4H), 7.02-7.45 (m, 4H), 6.69-6.92 (m, 2H).

HR-MS (ESI): $[M+H]^+$ $C_{25}H_{17}ClN_3O_5S$, calculated value 506.0577, measured value 506.0599.

Example 17

In this example, Compound 17, N-(2-(N-(quinoline-5-yl)aminosulfonyl)-pyridin-4-yl)-2-oxo-2H-chromene-8-amide, is prepared, which has a structure shown below:

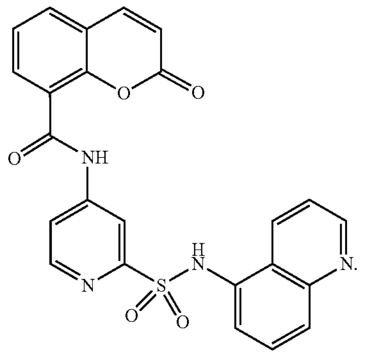 [SMILES: O=C(Nc1ccnc(S(=O)(=O)Nc2cccc3ncccc23)c1)c1cccc2ccc(=O)oc12]

The preparation method was carried out with reference to Example 1, wherein 4-chloroaniline was replaced with 5-aminoquinoline, to obtain a white solid (0.22 g, 34% yield). The product was characterized as follows:

$^1$H NMR (400 MHz, $CDCl_3$): δ 8.35-8.58 (m, 5H), 8.19 (m, 1H), 7.51-7.87 (m, 5H), 7.31 (m, 1H), 6.52 (m, 1H), 5.57 (m, 1H).

HR-MS (ESI): $[M+H]^+$ $C_{24}H_{17}N_4O_5S$, calculated value 473.0920, measured value 473.0934.

Example 18

In this example, Compound 18, N-(2-(N-(7-bromo-quinoline-5-yl)aminosulfonyl)-pyridin-4-yl)-2-oxo-2H-chromene-8-amide, is prepared, which has a structure shown below:

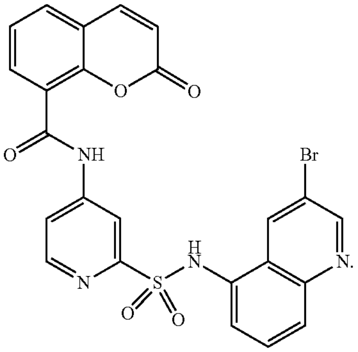

The preparation method was carried out with reference to Example 1, wherein 4-chloroaniline was replaced with 3-bromo-5-aminoquinoline, to obtain a white solid (0.24 g, 32% yield). The product was characterized as follows:

$^1H$ NMR (400 MHz, $CDCl_3$): δ 8.31-8.52 (m, 4H), 8.13 (m, 1H), 7.51-7.82 (m, 5H), 7.31 (m, 1H), 6.52 (m, 1H), 5.57 (m, 1H).

HR-MS (ESI): $[M+H]^+$ $C_{24}H_{16}BrN_4O_5S$ calculated value 551.0025, measured value 551.0043.

Testing Example 1

In vitro activity screening of SIRT2 inhibitors:

The full-length expression sequence ORF of the human SIRT2 gene is 1170 bp (Accession No.: NM_012237), and the molecular mass of the expressed SIRT2 protein is 43 KDa. The SIRT2 recombinant protein is expressed and purified according to the following steps: the SIRT2 gene was cloned into the expression vector pET-15b (primers were shown as follows: forward: 5[ -TAATACGACTCAC-TATAGGG-3[ (SEQ ID NO. 1); backward: 5[ -TT-CACTTCTGAGTTCGGCATG-3|| (SEQ ID NO. 2)), and the expressed SIRT2 protein contained $His_6$-tag at the N-terminus for purification. The plasmid was transformed into *E. coli* BL2 (DE3), and expressed for 6 h at 18° C. with 1 mM IPTG induction. The induced *E. coli* cells were collected by centrifugation and frozen at −20° C. Bacterial pellet was re-suspended in 15 mL of cell lysis buffer (50 mM Tris-HCl pH 8.0, 300 mM NaCl), and the bacterial sample was disrupted by sonication for 10 min, and then centrifuged (12000×g, 20 min) at 4° C. to remove the precipitates. The recombinant expression soluble SIRT2 protein existed in the supernatant.

The supernatant was purified by $Ni^{2+}$ NTA-agarose matrix column (Qiagen). In the purification process, the unbound proteins were first washed away with the loading buffer (50 mM Tris-HCl pH 8.0, 300 mM NaCl), subsequently, the non-specifically bound proteins were washed away by gradually increasing the concentration of imidazole (0-200 mM), and finally the purified recombinant SIRT2 protein was obtained. Imidazole was removed using a PD-10 column and the concentration of purified SIRT2 protein was determined by the Bradford method. The recombinant SIRT2 protein was stored at −20° C. in a preservation buffer (50 mM Tris-HCl, pH 8.0, 265 mM NaCl, 0.2 mM DTT, and 10% glycerol).

The SIRT2 enzyme activity assay is established based on the published studies. Firstly, peptide segment Ac-Gln-Pro-Lys-[Lys-(Ac)]-AMC, the substrate of SIRT2, was synthesized to serve as a substrate in the enzyme activity assay. The attached fluorescent label was AMC (7-Amino-4-methyl-coumarin). The whole assay includes two steps: the catalytic reaction was carried out in 60 μL of reaction solution (25 mM Tris-HCl, pH 8.0, 137 mM NaCl, 2.7 mM KCl, 1 mM $MgCl_2$ and 1 mg/mL BSA) with the addition of 500 μM $NAD^+$, 50 μM of substrate peptide, 1.0 μg of SIRT2, and Compounds 1-18 with different concentrations. The reaction was carried out at 37° C. for 2 hours. In this reaction, the acetyl group of Lysine residue on the small molecule peptide segment was removed to varying degrees. Afterwards, 60 μL of sample treating solution (50 mM Tris-HCl, pH 8.0, 100 mM NaCl, Trypsin and 4 mM nicotinamide) was added to the reaction solution and mixed, and placed at 37° C. for 20 min. Absorption intensity was measured by the enzyme-labeled instrument configured as an excitation light of 355 nm and an absorption light of 460 nm. In the assay, there were 2 parallel tests for each compound with each concentration, and a reasoned control was arranged, and the results were processed with software GraphPad Prism to calculate the inhibitory activity $IC_{50}$ of each inhibitor. The results are shown in Table 1 (in which AGK is the positive control group).

TABLE 1

| Compound | $IC_{50}$ μmol□$L^{-1}$ |
|---|---|
| 1 | 0.086 |
| 2 | 0.359 |
| 3 | 1.230 |
| 4 | 0.356 |
| 5 | 0.180 |
| 6 | 1.700 |
| 7 | 0.120 |
| 8 | 0.896 |
| 9 | 0.090 |
| 10 | 0.652 |
| 11 | 0.896 |
| 12 | 2.362 |
| 13 | 0.080 |
| 14 | 0.195 |
| 15 | 0.154 |
| 16 | 0.086 |
| 17 | 0.871 |
| 18 | 0.963 |
| AGK | 4.600 |

As can be seen from the data in Table 1: the in vitro SIRT2 inhibitory activity ($IC_{50}$) of all the eighteen compounds tested reaches the micromolar level, and in particular, $IC_{50}$ values of eleven compounds reach the $10^{-7}$ mol/L level, and $IC_{50}$ values of four compounds reach the $10^{-8}$ mol/L level, indicating that the 8-(picolinamide)-substituted coumarin compounds involved in the present application have good SIRT2 inhibitory activity.

Testing Example 2

Cytotoxicity assay of compounds for neuroblastoma cell SH-SY5Y:

This testing example investigates the cytotoxicity of compounds against neuroblastoma cell SH-SY5Y, in order to determine the dose for the Parkinson| s cell model protection assay in the next step. For the cytotoxicity assay, the specific test steps are as follows: the cultured neuroblastoma cell SH-SY5Y was grown in a 96-well cell culture plate with approximately 6000 cells per well. After overnight incubation, the culture medium was exchanged for a new one, and each well was added with different concentrations of Compounds 1-18 (0.01, 0.05, 0.1, 0.5, 1.5, 10, 20, 50, 100, 200 μM), and different control samples were arranged. The cells were continued to be incubated at 37° C. for 48 hours. Each well was added with 10 μL of the dye AlamarBlue® (Invitrogen), and the cells were continued to be incubated at 37° C. for approximately 2 hours and then a color change of the staining solution could be observed; the change of absorption values was obtained on the enzyme-labeled instrument (Ex: 530 nm; Em: 590 nm). In the assay, there were 2 parallel tests for each compound with each concentration. The results were processed with software GraphPad Prism to calculate the cytotoxicity $CC_{50}$ of each compound. The results are shown in Table 2 (in which Taxol is the positive control group).

TABLE 2

| Compound | $CC_{50}$ μmol□$L^{-1}$ |
|---|---|
| 1 | >20 |
| 2 | >20 |
| 3 | >20 |
| 4 | >20 |
| 5 | >20 |
| 6 | >20 |
| 7 | >20 |
| 8 | >20 |
| 9 | >20 |
| 10 | >20 |
| 11 | >20 |
| 12 | >20 |
| 13 | >20 |
| 14 | >20 |
| 15 | >20 |
| 16 | >20 |
| 17 | >20 |
| 18 | >20 |
| Taxol | 0.021 |

As can be seen from the data in Table 2: the cytotoxicity $IC_{50}$ of all the eighteen compounds tested against SH-SY5Y is greater than 20 μM, and i.e., the 8-(picolinamide)-substituted coumarin compounds involved in the present application do not have significant inhibitory activity against the SH-SY5Y cell.

Testing Example 3

Screening for compounds with protective activity on Parkinson□s disease cell model:

For the screening test for protective effects on the Parkinson□s disease cell model, the commonly recognized neurotoxicant $MPP^+$ (5 mM) is used on the neuroblastoma cell SH-SY5Y to construct the Parkinson□s disease cell model. This neurotoxicant acts on the SH-SY5Y cell, induces abnormal accumulation of α-synuclein in the cells and causes Parkinson□s disease-like neurotoxicity. The specific test method is as follows: approximately 20000 SH-SY5Y cells were grown in a 96-well cell plate and cultured overnight. The control test was carried out without neurotoxicant, and all other groups were added with neurotoxicant $MPP^+$ (5 mM) per well; the $MPP^+$ group did not add the protective compound; Compounds 1-18 (10 μM) were independently added to the culture wells of the protection assay (in which AGK was the positive control), and the incubation was continued for 48 h. The cell viability of the Parkinson□s disease cell model was determined to assess the protective effects of the compounds on the Parkinson□s cell model. The test data were analyzed by using GraphPad Prism. The results are shown in FIG. 1.

As can be seen from FIG. 1: all the eighteen compounds tested can protect the SH-SY5Y cell from the damage of $MPP^+$ neurotoxicant to a certain extent, indicating that the 8-(picolinamide)-substituted coumarin compounds involved in the present application have protective effects on neuroblastoma cells; among the compounds, Compounds 1, 13, 14 and 15 have more obvious protective effects on neuroblastoma cells.

The applicant declares that the 8-(picolinamide)-substituted coumarin compound of the present application, the preparation method therefor and the use thereof are illustrated in the present application through examples, but the present application is not limited to the examples, which means that the present application is not necessarily relied upon the examples to be implemented. It should be clear to those skilled in the art that any improvement of the present application, equivalent substitution of raw materials of the product of the present application and the addition of auxiliary ingredients, selection of specific methods, etc., shall all fall within the protection scope and disclosure scope of the present application.

The preferred embodiments of the present application are described in detail above, however, the present application is not limited to the specific details of the above embodiments. Within the scope of the technical conception of the present application, the technical solutions of the present application may have a variety of simple variations, and all the simple variations fall within the protection scope of the present application.

Additionally, it should be noted that the specific technical features described in the above embodiments can be combined in any suitable manner without contradiction, and in order to avoid unnecessary verbosity, the present application will not describe the various possible combinations.

What is claimed is:

1. An 8-(picolinamide)-substituted coumarin compound having a structure shown in Formula (I):

Formula (I)

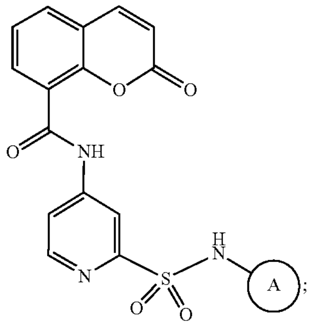

wherein, ring A is independently selected from the group consisting of: phenyl, naphthyl and a 5-14-membered aromatic heterocyclic group;

the phenyl, naphthyl and 5-14-membered aromatic heterocyclic group are unsubstituted or substituted with one to five $R_a$; each $R_a$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-8}$ alkoxy, $C_{1-8}$ alkylcarbonyl, $C_{1-8}$ alkoxycarbonyl, $C_{1-8}$ alkyl, $C_{3-8}$ cycloalkyl and phenyl;

for the $R_a$, the $C_{1-8}$ alkyl, $C_{3-8}$ cycloalkyl and phenyl are unsubstituted or substituted by one to five $R_b$; each $R_b$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino and $C_{1-8}$ alkylcarbonyl.

2. The 8-(picolinamide)-substituted coumarin compound according to claim 1, wherein in Formula (I), ring A is independently selected from the group consisting of: phenyl, naphthyl and a 5-14-membered aromatic heterocyclic group;

the phenyl, naphthyl and 5-14-membered aromatic heterocyclic group are unsubstituted or substituted with one to five $R_a$; each $R_a$ is independently selected from the group consisting of:

deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-6}$ alkoxy, $C_{1-6}$ alkylcarbonyl, $C_{1-6}$ alkoxycarbonyl, $C_{1-6}$ alkyl, $C_{3-6}$ cycloalkyl and phenyl;

for the $R_a$, the $C_{1-6}$ alkyl, $C_{3-6}$ cycloalkyl and phenyl are unsubstituted or substituted by one to five $R_b$; each $R_b$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino and $C_{1-6}$ alkylcarbonyl.

3. The 8-(picolinamide)-substituted coumarin compound according to claim 1, wherein the 8-(picolinamide)-substituted coumarin compound has a structure shown in Formula (IA):

Formula (IA)

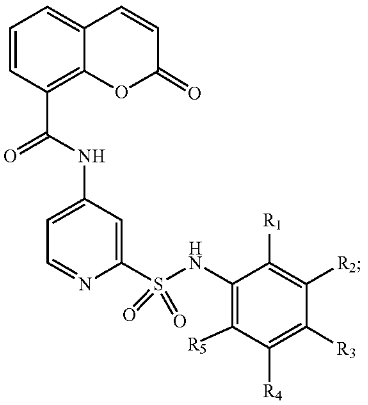

wherein, $R_1$, $R_2$, $R_3$, $R_4$ and $R_5$ are each independently selected from the group consisting of:

hydrogen, deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-4}$ alkoxy, $C_{1-4}$ alkylcarbonyl, $C_{1-4}$ alkoxycarbonyl, $C_{1-4}$ alkyl and phenyl.

4. The 8-(picolinamide)-substituted coumarin compound according to claim 1, wherein the 8-(picolinamide)-substituted coumarin compound has a structure shown in Formula (IB):

Formula (IB)

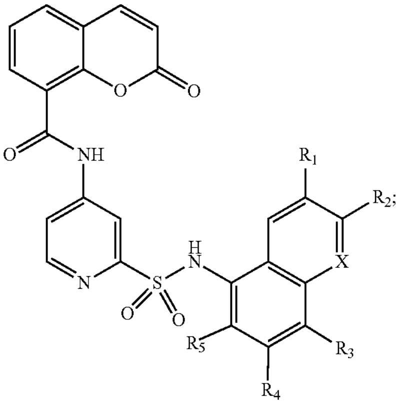

wherein, $R_1$, $R_2$, $R_3$, $R_4$ and $R_5$ are each independently selected from the group consisting of:

hydrogen, deuterium, halogen, hydroxyl, sulfhydryl, amino, cyano, nitro, methanesulfonyl, trifluoromethyl, trifluoromethoxy, formylamino, $C_{1-4}$ alkoxy, $C_{1-4}$ alkylcarbonyl and $C_{1-4}$ alkyl; and X is independently selected from N or C.

5. The 8-(picolinamide)-substituted coumarin compound according to claim 1, wherein the 8-(picolinamide)-substituted coumarin compound is selected from structures shown as follows:

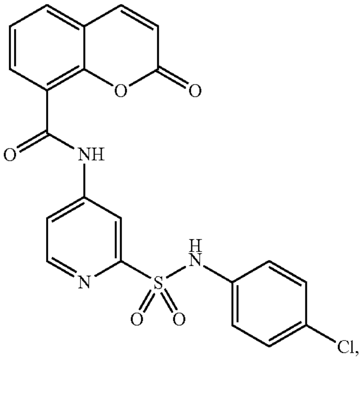

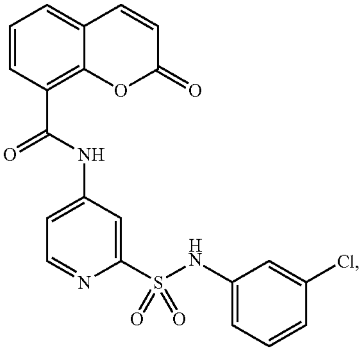

-continued

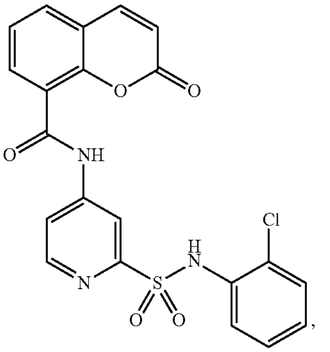

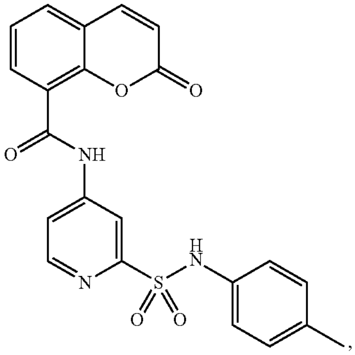

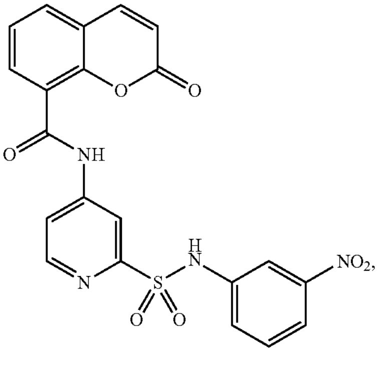

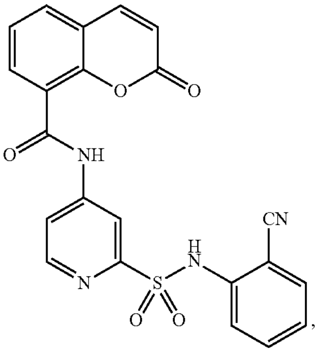

-continued
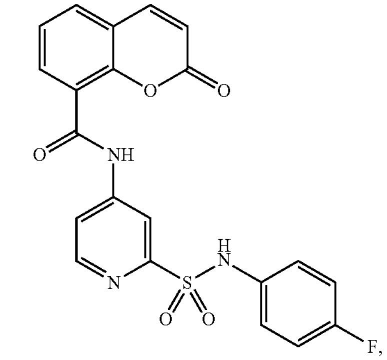
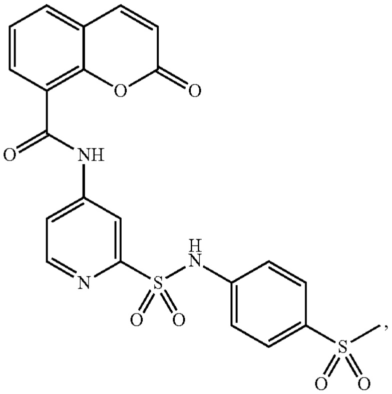
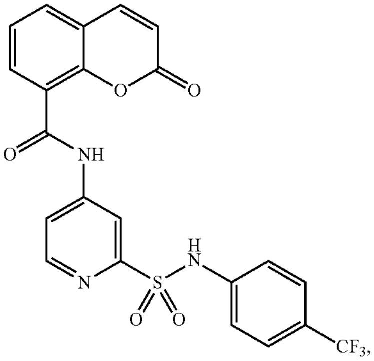
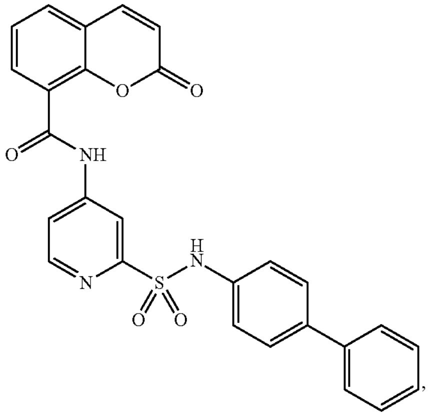
-continued
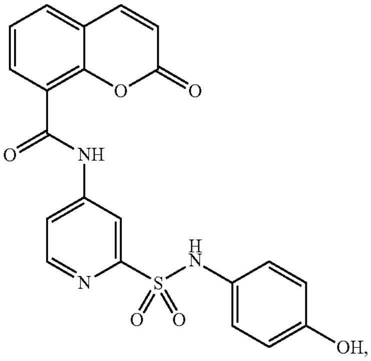
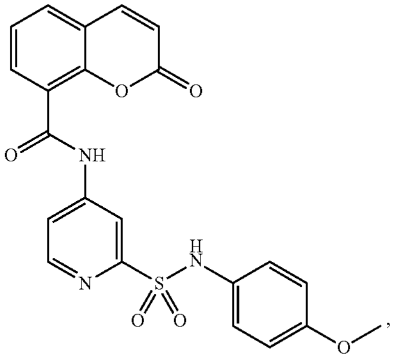
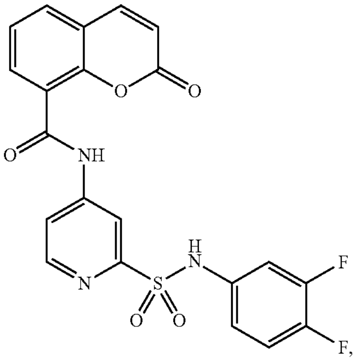
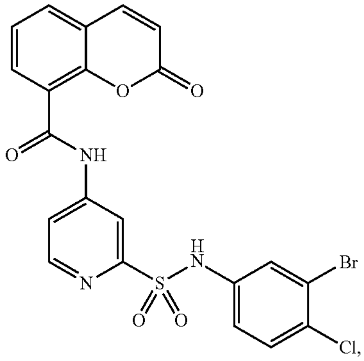

-continued

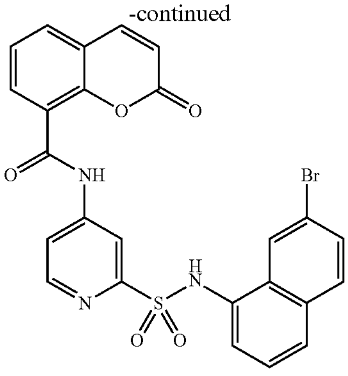

,

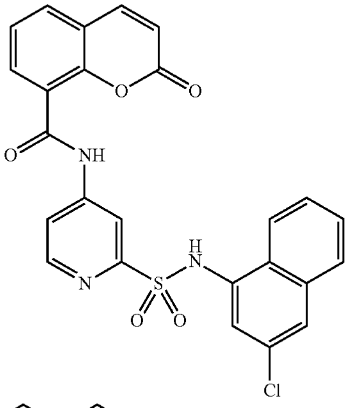

,

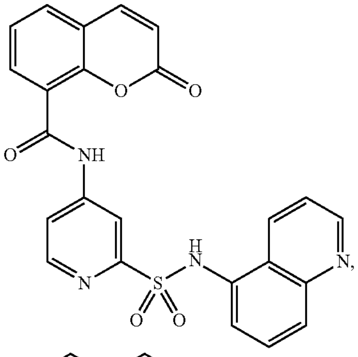

and

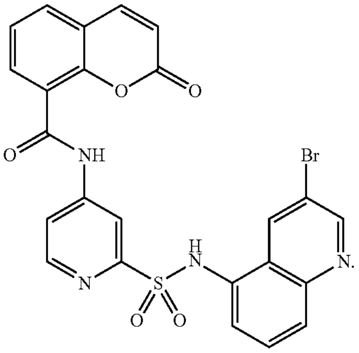 [SMILES: O=C(Nc1ccnc(S(=O)(=O)Nc2cccc3ncc(Br)cc23)c1)c1cccc2ccc(=O)oc12]

6. A stereoisomer of the 8-(picolinamide)-substituted coumarin compound according to claim 1, a pharmaceutically acceptable salt of the 8-(picolinamide) -substituted coumarin compound according to claim 1, or a pharmaceutical composition comprising the 8-(picolinamide)-substituted coumarin compound according to claim 1.

7. A pharmaceutical composition comprising the 8-(picolinamide)-substituted coumarin compound according to claim 1 and a pharmaceutically acceptable excipient.

8. A preparation method for 8-(picolinamide)-substituted coumarin compound, the method comprising:

mixing

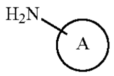

with DIPEA, and then mixing with 4-(2-oxo-2H-chromene-8-carboxamido)pyridine-2-sulfonyl chloride, and reacting to obtain 8-(picolinamide)-substituted coumarin compound of Formula (I), wherein ring A is independently selected from the group consisting of:

phenyl, naphthyl and a 5-14-membered aromatic heterocyclic group;

a reaction formula thereof is as follows:

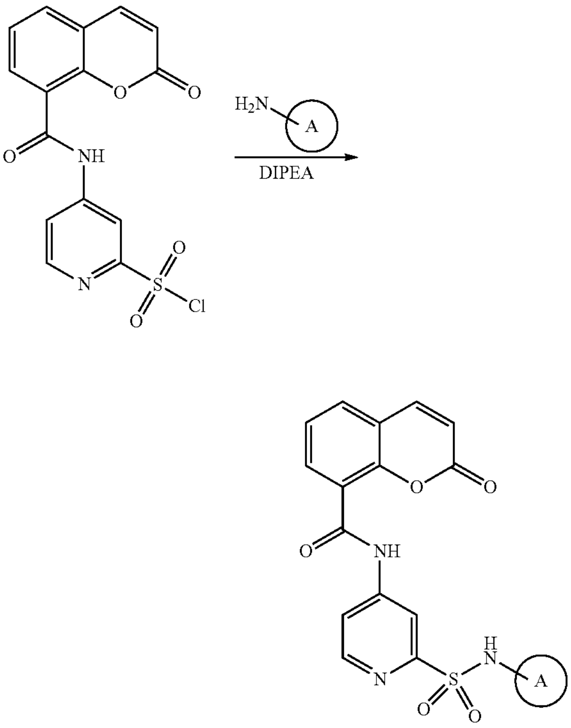

,

Formula (I) wherein:

the phenyl, naphthyl and 5-14-membered aromatic heterocyclic group are unsubstituted or substituted with one to five $R_a$; each $R_a$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino, $C_{1-8}$ alkoxy, $C_{1-8}$ alkylcarbonyl, $C_{1-8}$ alkoxycarbonyl, $C_{1-8}$ alkyl, $C_{3-8}$ cycloalkyl and phenyl; and for the $R_a$, the $C_{1-8}$ alkyl, $C_{3-8}$ cycloalkyl and phenyl are unsubstituted or substituted by one to five $R_b$; each $R_b$ is independently selected from the group consisting of: deuterium, halogen, hydroxyl, sulfhydryl, amino, cyano, nitro, azide, methanesulfonyl, isopropanesulfonyl, phenylsulfonyl, aminosulfonyl, methanesulfonate, isopropanesulfonate, phenylsulfonate, trifluoromethyl, trifluoromethoxy, formylamino and $C_{1-8}$ alkylcarbonyl.

9. The preparation method for the 8-(picolinamide)-substituted coumarin compound according to claim 8, wherein a preparation method for the 4-(2-oxo-2H -chromene-8-carboxamido)pyridine-2-sulfonyl chloride comprises the following steps:

(1) mixing 8-bromocoumarin with n-butyllithium, and then mixing with $CO_2$ gas under vacuum, and reacting to obtain coumarin-8-carboxylic acid;

(2) mixing coumarin-8-carboxylic acid with HATU and DIPEA, and then mixing with 4-aminopyridine-2-sulfonic acid, and reacting to obtain 4-(2-oxo-2H-chromene-8-carboxamido) pyridine-2-sulfonic acid; and (3) mixing 4-(2-oxo-2H-chromene-8-carboxamido)pyridine-2-sulfonic acid with thionyl dichloride, and reacting to obtain 4-(2-oxo-2H-chromene-8-carboxamido) pyridine-2-sulfonyl chloride;

a reaction formula thereof is as follows:

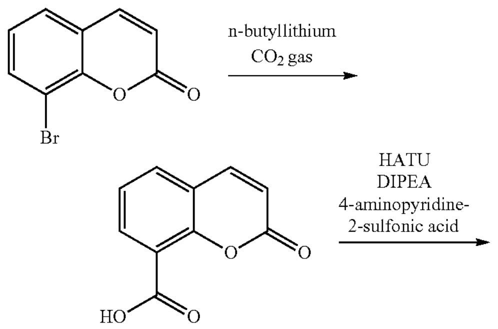

-continued

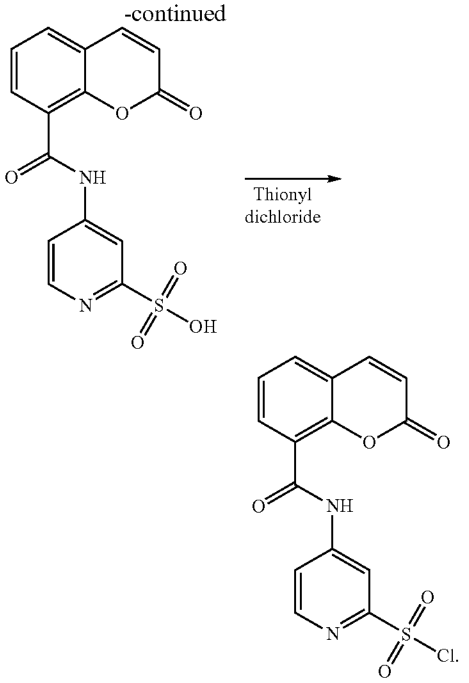

10. A method for treating a disease or a disorder associated with excessive SIRT2 activity or SIRT2 overexpression, the method comprising administering an effective amount of the 8-(picolinamide)-substituted coumarin compound according to claim 1 to subject in need thereof.

11. The method according to claim 10, wherein the disease or the disorder associated with excessive SIRT2 activity or SIRT2 overexpression comprises Parkinson's disease, metabolic disease or tumor.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1

-continued

```
taatacgact cactataggg                                              20


<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2

ttcacttctg agttcggcat g                                            21
```